United States Patent [19]
Bradshaw et al.

[11] Patent Number: 5,268,442
[45] Date of Patent: Dec. 7, 1993

[54] CHIRAL COPOLYMERS WITH OLIGOSILOXANE SPACERS

[75] Inventors: Jerald S. Bradshaw; Bryant E. Rossiter; Bryon J. Tarbet; Deborah F. Johnson, all of Provo; Milton L. Lee, Pleasant Grove, all of Utah; Karin E. Markides, Upsala, Sweden

[73] Assignee: Brigham Young University, Provo, Utah

[21] Appl. No.: 878,157

[22] Filed: May 4, 1992

Related U.S. Application Data

[63] Continuation-in-part of Ser. No. 612,269, Nov. 13, 1990, abandoned.

[51] Int. Cl.$^5$ .............................................. C08G 77/04
[52] U.S. Cl. ...................................... 528/25; 528/26; 528/28; 528/29; 528/30; 528/31; 556/419; 556/450
[58] Field of Search ................ 528/30, 31, 26, 28, 528/29, 25; 556/449, 450

[56] References Cited

U.S. PATENT DOCUMENTS 4,387,206 6/1983 Bayer et al. ............................. 528/28
4,997,965 3/1991 Lohmann et al. ..................... 556/419

*Primary Examiner*—Melvyn I. Marquis
*Attorney, Agent, or Firm*—Thorpe, North & Western

[57] ABSTRACT

Chiral copolymers containing chiral molecular grooves or cavities and oligosiloxane spacers are disclosed. The chiral portion of the copolymer is an enantiomerically enriched organic grouping, having physical properties attributed to uniform and stereochemically possible molecular grooves or cavities, which is chemically and thermally stable to gas, liquid or supercritical s fluid chromatographic conditions and is configured such that one enantiomer of an enantiomeric mixture will be better able to preferentially enter such groove or cavity and interact more strongly than other enantiomers in said mixture. The chiral grouping will contain one Or more combinations of organic moieties selected from the group consisting of methylene, phenylene, naphthylene, biphenylene, binaphthylene, a cyclodextrin and cycloalkylydene and substituted derivatives thereof and also includes non-metal atoms and functional groups which act as linking agents for the organic chiral cavity-containing moieties which are selected from the group consisting of ethers, thioethers, amines, carbonyls, amides, esters, sulfoxides, sulfonates, thioamides, thioesters, ureas, thioureas, carbamates, thiocarbamates, phosphines and phosphine oxides. The use of such polymers as chiral stationary phases in analytical and preparative gas, supercritical fluid and liquid chromatographic separations, and particularly for analysis of enantiomeric and other stereoisomeric mixtures of various substances is shown.

27 Claims, 10 Drawing Sheets

CHIRAL COPOLYMERS WITH OLIGOSILOXANE SPACERS

This application is a continuation-in-part of copending application Ser. No. 07/612,269 filed Nov. 13, 1990 and now abandoned.

BACKGROUND OF THE INVENTION

1. Field of the Invention

The present invention relates to novel chiral copolymers with oligosiloxane spacers and the use of such polymers as chiral stationary phases in analytical and preparative gas, supercritical fluid and liquid chromatographic separations. More particularly, this invention relates to novel chiral copolymers which contains chiral molecular cavities or chiral divalent linear molecules which could have a secondary structure possessing molecular grooves for use in chiral stationary phase separations. This invention also relates to the use of these copolymers for analysis of enantiomeric and other stereoisomeric mixtures of various substances. This invention relates as well to the use of either open tubular column surface-bonded or packed column particle-bound chiral copolymeric siloxane materials, prepared by coating and immobilizing by chemical reaction or heating the chiral copolymeric siloxanes on the desired column or particle surface for gas, supercritical fluid and liquid chromatography separations, and the separation of enantiomeric and other stereoisomeric mixtures of various structures using these materials.

2. Prior Art

Chiral chromatographic methods have become important as methods for determining enantiomeric excess and for preparatively resolving enantiomers. General references which discuss chiral phases and their uses are as follows: (1) W. A. König, "Separation of Enantiomers by Capillary Gas Chromatography with Chiral Stationary Phases," *J. Resolut. Chromatogr./Chromatogr. Commun.* (1982), v. 5, pp. 588-595; (2) R. H. Liu et al., "Chiral Stationary Phases for the Gas Liquid Chromatographic Separation of Enantiomers," *J. Chromatogr.* (1983), v. 271, pp. 309-323; (3) B. Koppenhoefer et al., "Chiral Recognition in Gas Chromatographic Resolution of Enantiomers on Chiral Polysiloxanes," *J. Chromatogr. Library* (1985), V. 32, pp. 1-42; (4) D. W. Armstrong et al., "Polar-Liquid, Derivatized Cyclodextrin Stationary Phases for the Capillary Gas Chromatography Separation of Enantiomers," *Anal. Chem.* (1990), v. 62, pp. 914-923; (5) K. Nakamura et al., "Chiral Polysiloxanes Derived from (R,R)-Tartaramide for the Gas Chromatographic Separation of Enantiomers," *Anal. Chem.* (1989), v. 61, pp. 2121-2124; (6) K. Nakamura et al., "Direct Resolution of Enantiomeric Diols by Capillary Gas Chromatography on a Chiral Polysiloxane Derived from (R,R)-Tartaramide," *Anal. Chem.* (1990), v. 62, pp. 539-541; and (7) V. Schurig and H.-P. Nowotny, "Gas Chromatographic Separation of Enantiomers on Cyclodextrin Derivatives," *Angewandte Chemie International Edition in English* (1990), V. 29, pp. 939-1076.

Three recent papers which describe the use of a chiral stationary phase in supercritical fluid chromatographic separations are (1) W. Roder et al., "Chiral SFC-Separations Using Polymer-Coated Open Tubular Fused Silica Columns. Comparison of Enantiomeric Selectivity in SFC and LC Using the Same Stationary Phase of the Pirkle Type," *J. High Resolut. Chromatogr./Chromatogr. Commun.* (1987), v. 10, pp. 665-667; (2) p. Macaudiere et al., "$CO_2$ Supercritical Fluid Chromatography with Chiral Phases: A Promising Coupling for the Resolution of Various Racemates," *J. Chromatogr. Sci.* (1989), V. 27, pp. 383-394; and (3) B.E. Rossiter et al., "The Rational Design of Chiral Stationary Phases for Capillary Supercritical Fluid Chromatography," *Tetrahedron Letters* (1991), v. 32, pp. 3609-3612. This latter paper describes chiral copolymers composed of a chiral hydrocarbon containing $C_2$ symmetry and an oligosiloxane spacer. These chiral copolymers are Similar to those described in this patent application except in the present case, the chiral portion of the copolymer is a chiral molecular groove or cavity.

Such methods rely on the presence of a chiral stationary phase (hereafter referred to as CSP) in the chromatographic system as a means of interacting with solutes such that one enantiomer of the solute emerges from the chromatographic system before the other, thus, separating the two enantiomers from each other. The first CSPs were developed for gas chromatography. Such CSPs were capable of resolving certain classes of racemates. They were limited in their utility in that the number of types of racemates they resolved was small and the CSPs, being low molecular weight organic compounds, had a pronounced tendency to bleed from the column even at relatively low temperatures (e.g., <200° C.). Thus they could resolve only a small number of volatile compounds. Since that time, effort directed towards the development of CSPs has largely had two objectives, i.e., to increase the selectivity of these materials so as to be able to separate the enantiomers of other types of racemates and to improve general chromatographic properties among which are thermal and chemical resiliency, low melting and high boiling points and high diffusion coefficients.

Because the mechanism for enantioselection Was and to a large degree still is incompletely understood, much of the effort directed towards CSP development centered more on an empirical effort to discover new types of functional group combinations capable of resolving enantiomers more than on incorporating desirable chromatographic properties. Even today, many types of CSPs for GC still have relatively poor chromatographic properties. Parallel development of achiral stationary phases for GC however demonstrated that the polysiloxanes have highly desirable characteristics for chromatographic separations. These qualities include low melting and high boiling points, high solute diffusion coefficients, and ease of properly distributing and immobilizing on chromatographic support materials. They can be anchored to fused silica surfaces in chromatographic columns through cross-linking processes, and can be deactivated, so as to promote extremely low volatility and high chemical and thermal stability. An important breakthrough came with the development of the CSP now known to as Chirasil-Val ™. This was first reported by H. Frank et al., "Rapid Gas-Chromatographic Separation of Amino Acid Enantiomers with a Novel Chiral Stationary Phase," *J. Chromatogr. Sci.* (1977), v. 15, pp. 174-179. This polymer incorporated features from both areas of development, i.e., desirable chromatographic properties and a pronounced ability to differentiate chromatographically different types of racemates. This material is characterized as being a polysiloxane possessing a certain percentage of pendant groups as chiral substituents whose purpose is to interact differentially with solutes.

This CSP has proven to be very popular for the separation of enantiomers of certain types of compounds. Similar CSPs have since been developed.

In spite of the great benefits of Chirasil-Val ™ and its sister CSPs, they have a major limitation. They are very specific with respect to the types of racemates they will resolve. The specificity of the CSP originates with the particular cluster of functional groups and the molecular structure of the chiral pendant arm. This limits their usefulness to the separation of only a limited number of enantiomers.

Certain alkylated cyclodextrins have been used for the separation of enantiomers in GC. These alkylated cyclodextrins have been diluted with polysiloxanes and coated on glass or fused silica columns as reported by H.P. Nowotny et al., "Extending the Scope of Enantiomer Separation in Diluted Methylated $\beta$-Cyclodextrin Derivatives by High Resolution Gas Chromatography," *J. High Resolut. Chromatogr.* (1989), v. 12, pp. 383-393; or lipophilic pern-pentylcyclodextrins and other similar peralkyl substituted cyclodextrins have been coated directly onto the column surfaces as discussed extensively in the aforementioned review by Schurig and Nowotny. These techniques have allowed enantiomeric separations of a variety of organic materials in GC at temperatures of 25 to 250° C. These materials have not been crosslinked or bonded to the glass or fused silica surfaces and so they cannot be used in GC at high temperatures (>250° C.) or in SFC or LC. In high temperature GC, these materials will bleed from the column surface and in SFC or LC, they will be washed from the column by the supercritical fluid or liquid.

Thus it will be recognized that what is needed in the art is an approach to CSP design that will produce CSP's with chiral resolving abilities, i.e. the ability to separate enantiomers and other stereoisomers, as well as excellent chromatographic properties, i.e. low and high operating temperatures, high solute diffusion with excellent separation properties at low temperatures, and that can be immobilized on a chromatographic column so that liquids or supercritical fluids will not strip or wash the phase off the columns. Similar phases which are stable to a wide variety of solvents and can be bound onto silica particles for liquid chromatography (LC) columns would also be an important addition to LC technology. Because it will be difficult or impossible to develop a single CSP which will resolve all classes of racemates, it is further desirable to be able to easily modify the CSP so as to accommodate different types of racemates while retaining desirable chromatographic properties. It is further desirable that the overall CSP design be such as to maximize the enantiomer resolving properties of the CSP. In this regard, it would be desirable to have these new CSPs contain chiral molecular grooves or molecular cavities, such as a cyclodextrin, which has a proven ability to separate all types of enantiomers, or chiral crown ethers or cyclams. Chromatographic phases having these novel properties for separating enantiomeric substances are disclosed and claimed in the present invention.

OBJECTS AND BRIEF SUMMARY OF THE INVENTION

It is, therefore, an objective of the present invention to provide novel chiral copolymers having properties for separating enantiomeric substances.

Another objective of the present invention is to provide novel Chiral copolymers which contain oligosiloxane spacers between the enantiomerically enriched organic units comprising chiral divalent linear molecules which could have a secondary structure possessing molecular grooves and/or cavities.

A further objective of the present invention is to provide novel chiral copolymers containing possible molecular grooves and/or cavities joined by oligosiloxane spacers which can be used as stationary phases for gas, supercritical fluid, and liquid chromatography.

It is a further objective of this invention to provide novel chiral copolymers containing possible chiral molecular grooves or cavities and oligosiloxane spacers which can be immobilized for use as stationary phases for gas, supercritical fluid, and liquid chromatography.

Yet another objective of the present invention is to provide superior methods for separating the enantiomers and other stereoisomers of various chemical compounds from mixtures thereof using gas-liquid chromatography.

An additional objective of the present invention is to provide superior methods for separating the enantiomers and other stereoisomers of various chemical compounds from mixtures thereof using liquid chromatography.

Still another objective of the present invention is to provide superior methods for separating the enantiomers and other stereoisomers of various chemical compounds from mixtures thereof using supercritical fluid chromatography.

These and other objectives and features of the present invention will be more fully apparent from the following description and appended claims, taken in conjunction with the accompanying drawings. However, in summary, the above stated objectives may be accomplished through the use of chiral copolymeric siloxanes having the following general formula:

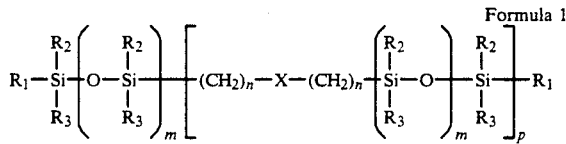

Formula 1

In the above formula 1, m is an integer from 1 to about 12, n is an integer from OZ about 16 and p is an integer from 1 to about 100; $R_1$, $R_2$ and $R_3$ are selected from the group consisting of lower alkyl, lower aryl, lower arylalkyl and chloro, nitro, or other substituents thereof which do not interfere with the functioning of these copolymeric siloxanes for their intended purpose and X is any chiral enantiomerically enriched organic grouping, having physical properties attributed to uniform and stereochemically possible molecular grooves or cavities, which is chemically and thermally stable to gas, liquid or supercritical fluid chromatographic conditions and is configured such that one enantiomer of an enantiomeric mixture will be better able to preferentially enter such groove or cavity and interact more strongly than other enantiomers in said mixture. X may be chiral as a result of possessing one or more stereogenic centers, axes and/or planes. By terminology such as "molecular groove", "possible molecular groove", "organic units comprising chiral divalent linear molecules which could have a secondary structure possessing molecular grooves", "pseudo molecular grooves" and the like is meant any structure which functions as if it wa physically configured such that one enantiomer of an enantiomeric mixture will be better able be better able to preferentially enter such groove or pseudo groove and interact more strongly than other enantiomers in said mixture. Because of the common functionality of these moieties, whether physically configured as molecular grooves or just functioning as such, i.e. pseudo molecular grooves, such structures shall be collectively referred to throughout this specification as "molecular groove(s)."

As noted above in Formula 1, the copolymers of the present invention are characterized as having alternating oligosiloxane and chiral enantiomerically enriched organic units containing molecular grooves or cavities. This polymeric arrangement of chiral organic units with molecular grooves or cavities between oligosiloxane spacer units is unique and the classes of polymers shown in Formula 1 are new and provide stationary phases which have superior enantiomeric separation abilities for certain classes of chiral organic compounds.

BRIEF DESCRIPTION OF THE DRAWINGS

All chromatograms shown are of separations on a stationary phase made in accordance with the present invention. These exemplify the ability of various embodiments of the invention to resolve enantiomers. FIGS. 1-3 illustrate separations using a molecular groove embodiment of the invention and FIGS. 4-illustrate separations using a molecular cavity embodiment.

FIG. 2A represents a separation of a racemic mixture. FIG. 2B represents separation of a crude synthetic mixture and FIG. 2C represents the separation of the (+) diol isomer.

FIG. 3 illustrates a supercritical fluid chromatogram of racemic diethyl tartrate.

DETAILED DESCRIPTION OF THE PREFERRED EMBODIMENTS

Figure 1A:
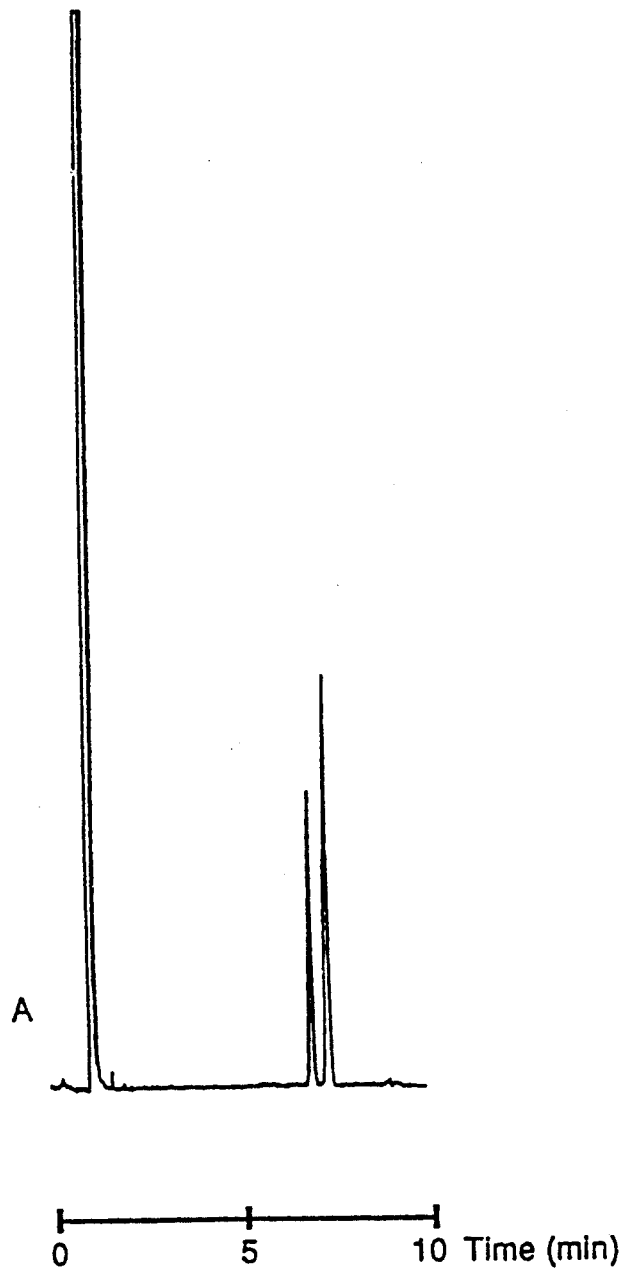
FIGS. 1A and 1B illustrates two gas chromatograms wherein enantiomers of the trifluoroacetamide derivatives of phenylethylamine and pentafluoropropionamide derivatives of naphthylethylamine were separated.

As referred to in the above summary, the novel chiral copolymers with oligosiloxane spaces having the following general formula:

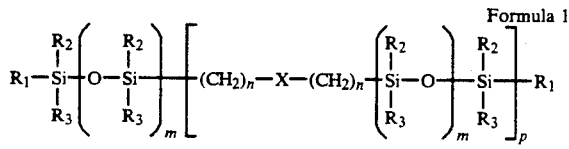

Formula 1

In the above Formula 1, m is an integer from 1 to about 12, n is an integer from 0 to about 16 and p is an integer from 1 to about 100; $R_1$, $R_2$ and $R_3$ are selected from the group consisting of lower alkyl, lower aryl, lower arylalkyl and chloro, nitro, or other substituents thereof which do not interfere with the functioning of these copolymeric siloxanes for their intended purpose and X is any chiral enantiomerically enriched organic grouping, having physical properties attributed to uniform and stereochemically possible molecular grooves or cavities, which is chemically and thermally stable to gas, liquid or supercritical fluid chromatographic conditions and is configured such that One enantiomer of an enantiomeric mixture will be better able to preferentially enter such groove or cavity and interact more strongly than other enantiomers in said mixture.

X may be chiral as a result of possessing one or more stereogenic centers, axes and/or planes. X is preferably configured to provide a cyclic or grooved organic grouping containing one or more combinations of organic moieties selected from the group consisting of methylene, phenylene, naphthylene, biphenylene, binaphthylene, a cyclodextrin and cycloalkylydene and substituted derivatives thereof.

In addition, to the organic and functional moieties, X may also include non-metal atoms and functional groups which can act as linking agents for the above named chiral cyclic or groove s containing organic moieties and may be selected from the group consisting of ethers, thioethers, amines, carbonyls, amides, esters, sulfoxides, sulfonates, thioamides, thioesters, ureas, thioureas, carbamates, thiocarbamates, phosphines and phosphine oxides. The total number of atoms possessed by X Will generally not exceed 300.

When X contains a molecular groove or is a linear arrangement of atoms which could have a secondary structure possessing a molecular groove, it is preferably an organic grouping containing one or more combinations of organic moieties selected from the group consisting of methylene, phenylene, naphthylene, biphenylene and binaphthylene.

When X contains a molecular cavity, it is preferably an organic grouping containing one or more combinations of organic moieties selected from the group consisting of biphenylene, binaphthylene, a cyclodextrin and cycloalkylydene and substituted derivatives thereof. Cyclodextrins or macrocycles are preferred. The chiral macrocycles may contain ether, thioether, amine, amide, ester and other known functional moieties which link hydrocarbons together. Cyclodextrins and cyclic polyethers or amines are particularly preferred.

The term "substituted derivatives" or "substituents", when used, applies to substituents which may be attached to the various organic groupings represented by X or to the lower alkyl, lower aryl, lower arylalkyl groups represented by $R_1$, $R_2$ and $R_3$ which do not interfere with the functionality of these groups in the present invention. It serves no useful purpose to attempt to list each substituent which may be present as such will either be obvious to those skilled in the art or may be empirically determined without undue experimentation.

The above requirements for the X group in the copolymers outlined in this invention are exemplified by typical formulas for X shown in Formula 2 through Formula 7. These formulas are exemplary only and are not intended to be an extensive listing of all chiral organic moieties which may serve as molecular grooves. In Formula 3 the term "Bz" stands for benzoyl (—C-

(O)C$_6$H$_5$) and in Formula 7 "Ph" stands for phenyl (—C$_6$H$_5$).
Formula 2
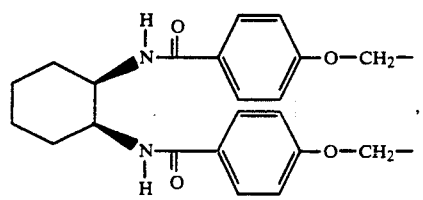
Formula 3
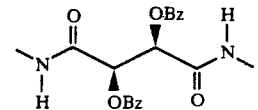
Formula 4
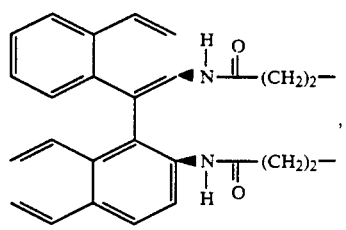
Formula 5
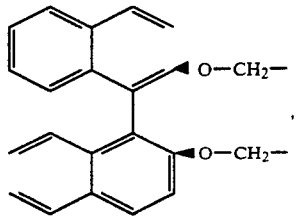
Formula 6
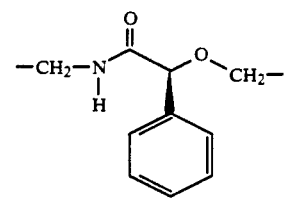
and
Formula 7
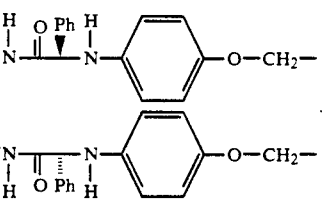
As a second embodiment, where X is a molecular cavity with chiral positions on the cavity, some possible formulas are showing in Formulas 8-12. These formulas are exemplary only and are not intended to be an extensive listing.
Formula 8
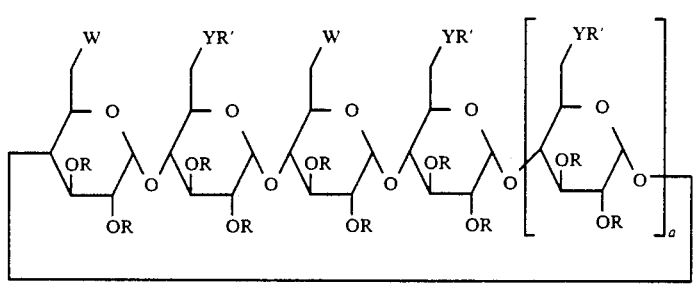
Formula 9
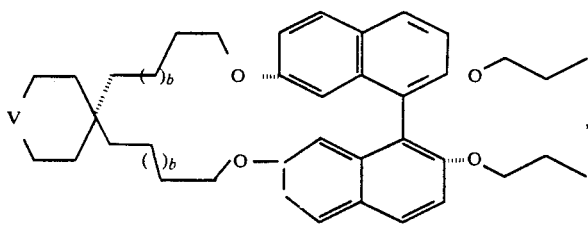
Formula 10
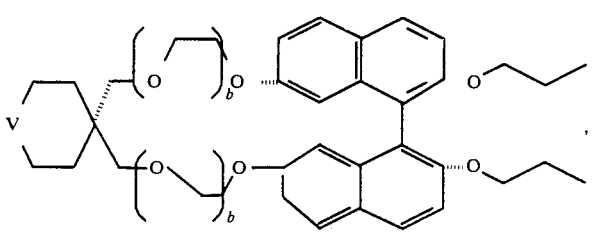

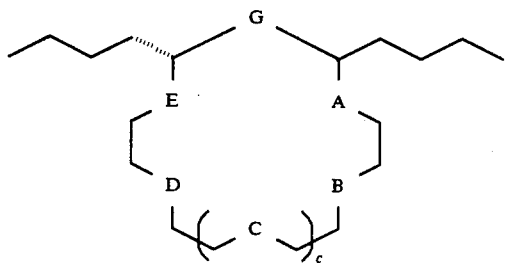

Formula 11 and

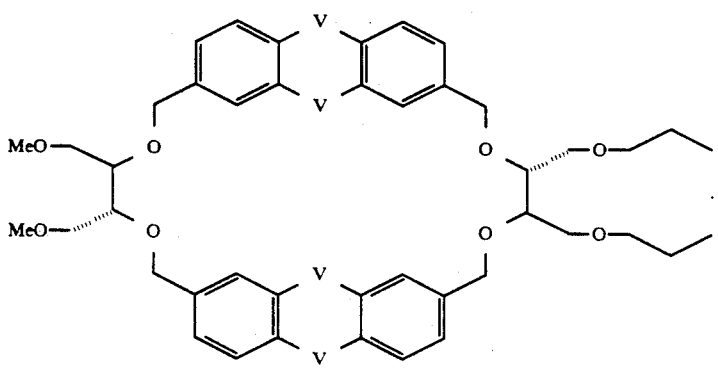

Formula 12

In Formula 8, a cyclodextrin, R is a member selected from the group consisting of H, alkyl, aryl or aralkyl and is preferably H or lower alkyl with methyl or n-pentyl being particularly preferred. W is a linking group to connect the cyclodextrin to the silane spacers and is a member selected from the group consisting of —O—, —S—, —O—Ar—O—, —S—Ar—S—, —S—Ar—O—, —O—Ar—S, —O—Ar—, —S—Ar—, —NHC(O)—, —NHC(S)—, —N(R')—, —N(R')—Ar—O—, —N(R')—Ar—S—, —N(R')—Ar—, —NHC(O)—Ar—O—, —NHC(O)—Ar—, —NHC(O)—Ar—S—, —O—Ar—NH-C(O)—, —S—Ar—NHC(O)—, and the like where Ar is an aromatic ring selected from the group consisting of phenylene, pyridylene, and furanylene and R' is a member selected from the group consisting of H, alkyl, aryl and aralkyl with alkyl being preferred. Particularly preferred groups for W are —O—p—C₆H₄O—, —NH-C(O)—p—C₆H₄O—, and —NHC(O)—p—C₆H₄—. YR' is representative of a variety of moieties consisting of alcohols, thiols, ethers, esters, thioethers, thioesters, amines, amides, thioamides and the like with Y being a member selected from the group consisting of O, OC(O), S, SC(S), NHR', NHC(O), NHC(S) and the like and R' being a member selected from the group consisting of H, alkyl, aryl and aralkyl with alkyl being preferred. The integer "a" can vary from 2 to 4 with 3 being preferred.

In Formulas 9, 10 and 12, V can be a member selected from the group consisting of CH₂, O, S, NR", C(O), NC(O)R", NC(S)R" and the like where R" is a member selected from the group consisting of H, alkyl, aryl and aralkyl with alkyl being preferred. The integer "b" may vary from 0 to 10 and, when not zero, is preferably 1-10. In Formula 12, V can be the same or different.

In Formula 11, A-E can be any member, or combination of members, selected from the group consisting of O, CH₂O, S, CH₂S, NR" or CH₂NR" where R" is a member selected from the group consisting of H, alkyl, aryl and aralkyl with alkyl being preferred. G may be a member selected from the group consisting of CH₂OCH₂, CH₂SCH₂, CH₂N(R")CH₂, phenylene, pyridylene and furanylene. The integer "c" may vary from 0 to 6 and, when not zero, is preferably 1-3.

Again, it should be emphasized that any of the hydrocarbon groupings represented by Ar, R, R' or R" can contain substituents which do not interfere with the functional operation of the copolymers in effecting separations. Typical or representative substituents will be inclusive of chloro, bromo, fluoro, nitro and the like.

As previously referred to, the copolymers represented by Formula 1, are characterized as having alternating oligosiloxane and chiral enantiomerically enriched organic units configured as molecular cavities or grooves. This polymeric arrangement of chiral organic units containing molecular cavities, molecular grooves or possible (pseudo) grooves between oligosiloxane units is unique. These novel classes of polymers provide stationary phases which have superior enantiomeric separation abilities for certain classes of chiral organic compounds.

It can be conceived that polymers of Formula 1 discriminate on the basis of shape. Such a phase would be characterized as one which is capable of interaction between the CSP and solute, but which contains possible chiral grooves or cavities such that, in order to interact with the CSP, the solute must enter to some degree into that groove or cavity. In principle, one solute enantiomer will be better able to enter that groove or cavity than the other in order to interact more strongly. Indeed, the substituents forming the groove or cavity may also be those with which the solutes interact. In order for such chiral recognition to occur, these grooves or cavities must be uniform and stereochemically possible.

A good CSP should integrate material properties considered desirable for gas, supercritical fluid, and liquid chromatography in general, as well as the ability to resolve enantiomers, so that one has a chromatographic system which not only is capable of resolving a wide range of enantiomers, but also manifests high efficiency over wide temperature range, long column life, high degree of reproducibility, and good sample capacity.

In this regard, it has been discovered that polymers of Formula 1 exhibit good selectivity, good efficiency and are operable within a wide temperature range. In particular, the novel chiral copolymers of the present invention have shown superior utility in separating the stereoisomers of, for example, 1,2-diols and acetylated amines, not only due to the selectivity of the stationary phase but also from the high efficiency created by the siloxane blocks in the copolymer.

In Formula 1 above, n can be an integer from 0 to about 16 with 2 to about 10 being preferred and 2 and 8 being particularly preferred. $R_1$, $R_2$ and $R_3$ are selected from the group consisting of lower alkyl, lower aryl and lower arylalkyl with alkyl being preferred. The most preferred embodiment is $R_1$ being octyl and $R_2$ and $R_3$ being methyl. Therefore, in one particular preferred embodiment n is 2, $R_1$ is octyl and $R_2$ and $R_3$ are methyl. In another particularly preferred embodiment has n is 8, $R_1$ is octyl and $R_2$ and $R_3$ are methyl.

The value of m in Formula 1 is an integer from 1 to 12 with 1 to 5 being preferred and with 1 and 3 being the most preferred. The value of p in Formula 1 is an integer from 1 to 100 with 35-50 being the most preferred. However, it will be appreciated that the precise value of p will depend on the particular application involved, with the optimum value of p depending on such factors as the desired efficiency and solubility of the resulting copolymer.

The preferred embodiments for X, functioning as a molecular groove, i.e. a divalent linear structure possibly including a secondary structure having a chiral groove, are shown by the structures in Formulas 2-7 shown above. The most preferred molecular groove embodiments for X are shown by the structures in Formulas 2, 3 and 4.

The preferred embodiments for X, as a molecular cavity, are shown by the structures in formulas 8-12. The most preferred embodiments for X, as a molecular cavity, are shown by the structures in Formula 8.

As they pertain to the linear structure embodiments functioning as a molecular groove, representative compounds within the scope of the invention which are illustrated in the follow examples are (1) m=3, n=2, p=about 42, $R_1$=octyl, $R_2$ and $R_3$ =methyl and X=the chiral structure shown in Formula 2; (2) m= 1, n=2, p=about 46, $R_1$=octyl, $R_2$ and $R_3$=methyl and X=the chiral structure shown in Formula 2; (3) m=3, n=2, p=about 40, $R_1$=octyl, $R_2$ and $R_3$=methyl and X=the chiral structure shown in Formula 3; (4) m=3, n=8, p=about 36, $R_1$=octyl, $R_2$ and $R_3$ =methyl and X=the chiral structure shown in Formula 4; and (5) m=1, n=2, p=about 40, $R_1$=octyl, $R_2$ and $R_3$=methyl and X=the chiral structure shown in Formula 4.

As it pertains to the molecular cavity embodiment, a representative compound within the scope of the invention which is illustrated in a following example is where m=5, n=3, p=about 13, $R_1$=octyl, $R_2$ and $R_3$=methyl, and X=the Chiral structure shown in Formula 8 where W is=O—p—$C_6H_4O$, and YR'-=$OCH_3$, and R is methyl. Other compounds within the scope of the invention have the same structure as above except YR' are $OC_5H_{11}$ or $OCH_3$, and R is $C_5H_{11}$ or $CH_3$ or a mixture of $C_5H_{11}$ and $CH_3$. Another example is the same as the one mentioned above except W is NHC(O)—p—$C_6H_4O$.

The preferred procedures to prepare the copolymers in accordance with Formula 1 and which contain molecular grooves are outlined in Procedure I below and in Examples 1-5 which follow.

PROCEDURE I

In this procedure, an appropriate dialkene-containing chiral organic moiety is first prepared as shown in Equation 1 for the preparation of 1,2-bis-4'-allyloxybenzamidocyclohexane. In this regard, the appropriate alkene-containing acid chloride is reacted with the chiral diamine in an appropriate solvent such as pyridine, benzene or tetrahydrofuran (THF). An excess of base such as triethylamine or 4-methyl morpholine must be used in solvents other than pyridine.

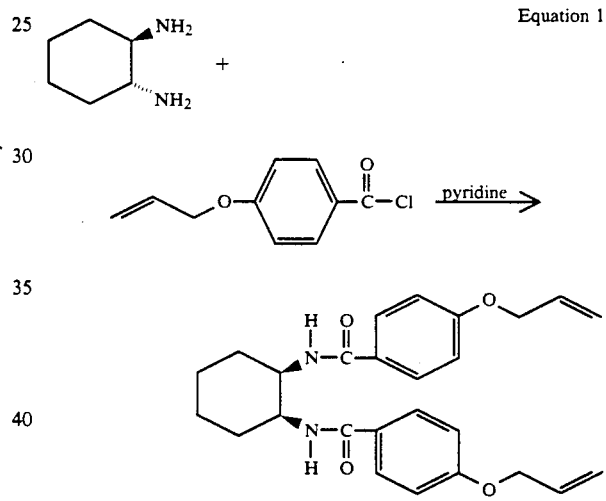

Equation 1

The reaction mixture is stirred at room temperature for a few hours and can be refluxed for a few hours if necessary to effect the reaction. The mixture is cooled and is usually added to water and the dialkene-containing chiral diamide is extracted into a suitable organic solvent such as chloroform or ether. Often the chiral diamide reaction mixture is evaporated rather than added to water. In this case, the crude product is dissolved in the appropriate solvent. In either case, the solvent is dried over anhydrous sodium or magnesium sulfate and evaporated. The product is then purified by recrystallization from an appropriate solvent if it is a solid or, if it is a liquid, by column chromatography or preparative HPLC on silica gel using the appropriate mixture of solvents such as chloroform, hexane and ethyl acetate as eluent. In addition to chiral 1,2-bis-4'-allyloxybenzamidocyclohexane shown in Equation 1, other chiral dialkene-containing diamides, corresponding to Formulas 3 and 4, that were prepared by similar procedures and used to prepare copolymers in accordance with Formula 1 are shown below.

13

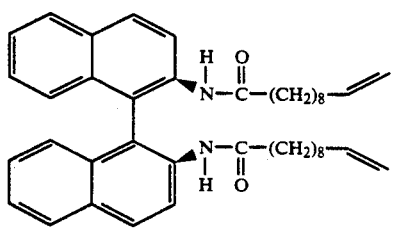

14
-continued

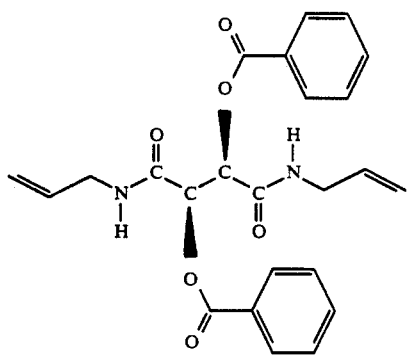

In the second step of Procedure I, the dialkene-containing chiral diamides prepared above are reacted with an oligosiloxane containing a Si(CH₃)₂H unit on each end such as 1,1,3,3-tetramethyldisiloxane or 1,1,3,3,5,5,7,7-octamethyltetra siloxane (both purchased from Petrarch Systems, 2731 Bartram Road, Bristol, PA 19007 and distilled prior to use). The reactions to form two copolymers in accordance with Formula 1 are given in Equations 2 and 3.

Equation 2

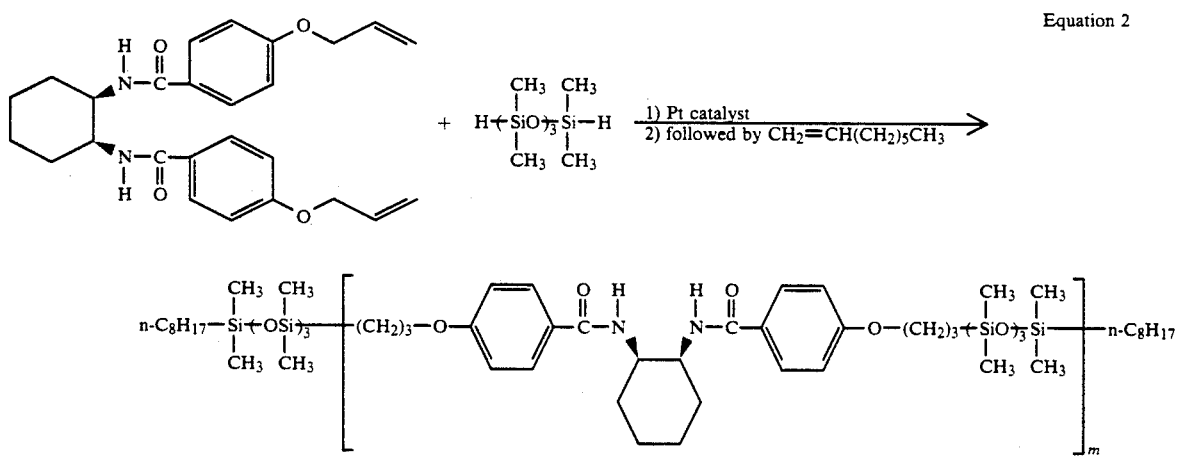

Equation 3

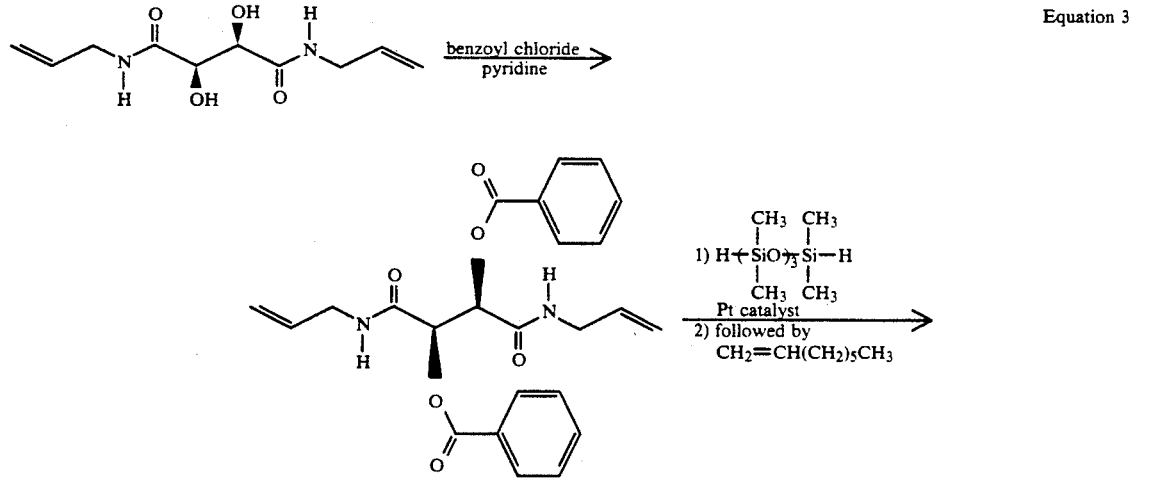

-continued

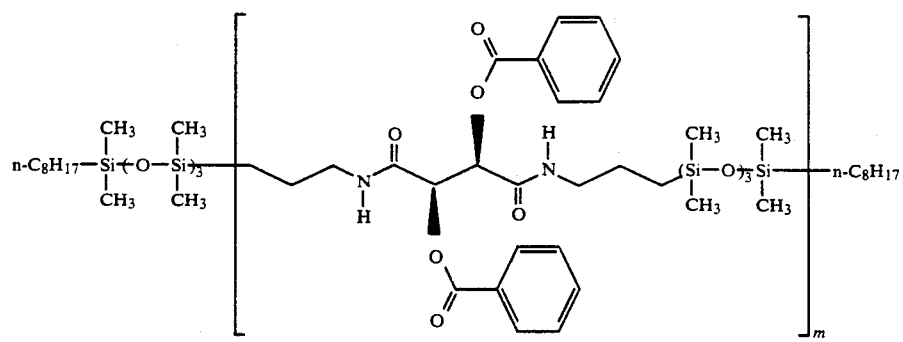

In Equations 2 and 3, the oligosiloxane reactant used is 1,1,3,3,5,5,7,7-octamethyltetrasiloxane. It is possible to use a dodecamethylhexasiloxane analog or other similar analogs or a mixture of analogs for this reaction.

In regard to the reactions shown in Equations 2 and 3, a mixture of an excess of the siloxane, platinum catalyst (which can be any suitable platinum material such as hexachloroplatinic acid hydrate or dicyclopentadienyl platinum) a known amount of 1-octene for end capping purposes to give the correct molecular weight to the copolymer) and 10 mL of toluene are placed in a small Teflon centrifuge tube. After heating the capped tube for about 2 hours, the tube is cooled and the appropriate amount of dialkene-containing chiral diamide is added and the tube is closed and the mixture stirred by appropriate means at 50° C. until the polymerization reaction is completed. Stirring can be by a magnetic stirring bar or by sonic means. The reaction is followed by observing the decrease in the intensity of the Si-H absorption in infrared spectroscopy. When the bond is no longer seen, the reaction is complete. This takes 2 to 50 hours or even longer. Often, additional platinum catalyst must be added. The toluene is evaporated in a stream of nitrogen or argon gas. The resulting polymer is dissolved in a minimum amount of methylene chloride (usually about 10 mL per gram) and precipitated with methanol or methanol and water. The mixture is centrifuged, the solvents decanted and the precipitate is again dissolved in methylene chloride. This process of dissolution in methylene chloride and precipitation with methanol or methanol and water is repeated 3 or 4 times to ensure separation of the polymer from the unreacted alkene. The polymer is then dissolved in methylene chloride and filtered through a 0.2 mm filter. The solvent is then removed and the polymer is dried under vacuum at 0.1 torr to 1 torr at 50°-60° C. for a period of 12 to 24 hours.

The following examples are given to illustrate various copolymers which have been made or may be made containing molecular grooves in accordance with Formula 1 of the present invention. These examples are illustrative only and are not comprehensive of the many different copolymers which can be made in accordance with this embodiment.

EXAMPLE 1

In this example, a copolymer gum within the scope of Formula 1 was made wherein m=3, n=2, p=about 42, $R_1$=octyl, $R_2$ and $R_3$ =methyl and X=the chiral structure shown in Formula 2.

In this regard, chiral trans-1,2 -bis-4'-allyloxybenzamidocyclohexane (see Equation 1) was first prepared as follows. Oxalyl chloride (4.3 g, 33.9 mmole) was added to a suspension of 5.09 g (28.1 mmole) of 4-allyloxybenzoic acid (prepared from allyl bromide and 4-hydroxybenzoic acid) in 70 mL of benzene at room temperature. The reaction mixture was stirred for 10 min at room temperature followed by refluxing until the acid dissolved (10-15 min). The solvent was removed under reduced pressure to give an oily residue, which was dissolved in 60 mL of THF. 4-Methylmorpholine (3.4 g, 33.7 mmole) was added to the reaction mixture at 0° C. under an argon atmosphere. A solution of 1.15 g (10.1 mmole) of chiral trans-1,2-diaminocyclohexane (Fluka Chemical Corp., 980 South Second Street, Ronkonkoma, NY 11779) in mL of THF was added to the reaction mixture at room temperature. The reaction mixture was stirred for 10 min at room temperature followed by refluxing for 2 hours. The reaction mixture was evaporated under reduced pressure to give a solid residue, which was dissolved in 200 mL of chloroform. The chloroform solution was washed with 100 mL of water, 100 mL of 1 N aqueous HCl, twice with 150 mL portions of 5% aqueous $Na_2CO_3$, and again with 100 mL of water. The chloroform layer was dried over anhydrous sodium sulfate and evaporated under reduced pressure to give a crude product, which was purified by preparative HPLC (silica gel, chloroform-/ethyl acetate=3/1). The resulting White solid was recrystallized from ethyl acetate-hexane to give 2.47 g (56%) of product; $[\alpha] - 125.88°$ (c=3.98, $CH_2Cl_2$); mp 159°-161° C.; NMR (CD $Cl_3$) δ 1.45 (m, 4 H), 1.82 (m, 2 H), 2.20 (m, 2 H), 4.0 (m, 2 H), 4.45 (dd, 4 H), 5.20-5.50 (dd, 4 H), 5.9-6.1 (m, 2 H), 6.75 (d, 4 H), 6.9 (m, 2 H), 7.65 (d, 4 H); IR (K Br) 3297, 3083, 1685, 841, 767 $cm^{-1}$.

The copolymer (see Equation 2) was prepared by heating a mixture of 0.23 g (0.83 mmole) of 1,1,3,3,5,5,7,7-octamethyltetrasiloxane, a trace (several crystals) of dicyclopentadienyl platinum, 7.02 microliters of 1-octene and 10 mL of toluene in a tightly capped 50 mL Teflon centrifuge tube in a sonic bath (Branson 2200) at 50° C. for two hours. The amount of 1-octene used in the reactions was designed to give a final copolymer molecular weight of about 25,000. The heated mixture was cooled and 0.34 g (0.78 mmole) of chiral trans-1,2-bis-4'-allyloxybenzamidocyclohexane was added. The tube was capped and heated in the sonic bath at 50° C. for 15 hours. An infrared spectrum of the mixture showed no Si—H bonds, indicating that the reaction was complete. The toluene was evaporated in a nitrogen gas stream and the copolymer residue was dissolved in 10 mL of methylene chloride, and 10 mL of methanol and 20 mL of water were added. The mixture was centrifuged and the solvents were decanted. The process of dissolution in methylene chloride and precipitation by methanol and water was repeated three more times. The copolymer was dissolved in 10 mL of methylene chloride and filtered through a 0.2 mm filter. The solvent was evaporated giving 0.53 g (64%) of brown crystalline copolymer which was dried under vacuum at 60° C. for 18 hours.

EXAMPLE 2

In this example, a copolymer gum within the scope of Formula 1 was made wherein m=1, n=2, p=about 46, $R_1$ octyl, $R_2$ and $R_3$ =methyl and X=the chiral structure shown in Formula 2.

The copolymer of Example 2 was prepared exactly as the copolymer of Example except 0.11 g (0.85 mmole) of 1,1,3,3-tetramethyldisiloxane was used in Example 2 rather than 0.23 g (0.83 mmole) of 1,1,3,3,5,5,7,7-octamethyltetrasiloxane which was used in Example 1. The resulting copolymer (0.38 g, 86%) was a brown crystalline material.

EXAMPLE 3

In this example, a copolymer gum within the scope of Formula 1 was made wherein m=3, n=2, p=about 40, $R_1$=octyl, $R_2$ and $R_3$ =methyl and X=the chiral structure shown in Formula 3.

In this regard, chiral O, O-dibenzoyl-N, N'-diallyltartardiamide was first prepared (see Equation 3). N, N'-diallyltartardiamide (Aldrich Chemical Company, Inc., 1001 West St. Paul Ave, Milwaukee, WI 53233) (4.6 g, 20 mmole) was dissolved in 50 mL of pyridine and treated with 12.49 (88 mmole) of benzoyl chloride at room temperature. After several hours, the reaction mixture Was poured into ice water and the water Was extracted with ether, and the ether layer was discarded. The water was treated with 3N aqueous HCl which resulted in the formation of a white precipitate. The mixture was filtered and the white precipitate washed With water and then ether giving, after drying in an oven, 8.3 g of a white powder, mp=194°-197° C. The product was further purified by refluxing in ether, cooling the mixture and filtering to give 7.3 g of a white powder which was dried at 100° C.; mp 196-197° C.; [α]−78.6 (CHCl$_3$, c=2.26); NMR (CD Cl$_3$) δ3.7-4.0 (m, 6 H), 4.9-5.2 (dd, 4 H), 5.6-5.8 (m, 2 H), 6.45 (t, 2 H), 7.4 (t, 4H), 7.6 (m, 2 H), 8.05 (d, 4 H); IR (KBr) 3361, 3093, 2921, 1724, 1694, 719 cm$^{-1}$.

The copolymer (see Equation 3) was prepared by heating a mixture of 0.26 g (60 mmole) of O,O'-dibenzoyl-N,N'-diallyltartardiamide, 0.17 g (61 mmole) of 1,1,3,3,5,5,7,7-octamethyltetrasiloxane, a trace of hexachloroplatinic acid hydrate, 10 microliters of 1-octene and 10 mL of toluene at 50° C. in a stoppered Teflon centrifuge tube in a sonic bath for 15 hours. The infrared spectrum of the mixture showed that many of the Si—H units had not reacted. An $^1$H NMR spectrum showed about 36% of the alkene units also had not reacted. Additional hexachloroplatinic acid hydrate was added to the mixture and the reaction was carried out for an additional 24 hours. The toluene was evaporated under a nitrogen stream and the copolymer was dissolved in 10 mL of methylene chloride and 10 mL of methanol, and 20 mL of water were added. The mixture was centrifuged and the solvents were decanted. The process of dissolution in methylene chloride and precipitation by methanol and water Was repeated three more times. The copolymer was dissolved in 10 mL of methylene chloride and filtered through a 0.2 mm filter. The solvent Was evaporated giving 0.37 g (86%) of a light yellow crystalline material which was dried at 0.1 torr at 60° C. for 18 hours.

EXAMPLE 4

In this example, a copolymer gum within the scope of Formula 1 was made wherein m=3, n=8, p=about 36, $R_1$=octyl, $R_2$ and $R_3$ =methyl and X=the chiral structure shown in Formula 4.

In this regard, (S)-2, 2'- bis(10-undecenamide)-1,1'-binaphthalene first prepared. (S)-1,1'-binaphthalene-2,2'-diamine was dissolved in 5 mL of dichloromethane and 1 mL cf pyridine. To this solution was added 2.5 g (12.4 mmole) of 10-undecenoyl chloride (Aldrich Chemical Co.). The reaction mixture was stirred at room temperature for 90 minutes. The reaction mixture was then poured into water and the mixture was extracted with diethyl ether. The ether extract was washed twice with aqueous 1N hydrochloric acid, once with saturated aqueous sodium s bicarbonate and dried over anhydrous sodium sulfate. The ether extract was concentrated to give an oil. This oil was purified chromatographically on silica gel using an eluting solvent mixture consisting of 10% ethyl acetate/90% hexane to give the dienediamide product as an oil; $[\alpha]_d$ =52.9 (c=6.14, CH$_2$Cl$_2$); $^1$NMR (CD Cl$_3$) δ 0.9-1.4 (m, 24 H), 1.55 (s, 2 H) 1.9-2.1 (m, 8 H), 4.8-5.0 (dd, 4 H), 5.7-5.9 (m, 2 H), 6.9-7.3 (m, 4 H), 7.4 (t, 2 H), 7.8-8.1 (m, 4 H), 8.38 (d, 2 H).

The copolymer was prepared by heating a mixture of 0.40 g (0.64 mmole) of (S)-2,2'-bis(10-undecenamido)-1,1'-binaphthalene, 0.20 g (0.69 mmole) of 1,1,3,3,5,5,7,7-octamethyltetrasiloxane, a trace of hexachloroplatinic acid hydrate, 10 microliters of 1-octene and 10 mL Of toluene at 50° C. in a stoppered Teflon centrifuge tube in a sonic bath for 15 hours. The mixture was then treated exactly as reported above in Example 3 to give 0.91 g of o copolymer which contained some occluded solvent.

EXAMPLE 5

In this example, a copolymer gum within the scope of Formula was made wherein m=1, n=2, p=about 40, $R_1$=octyl, $R_2$ and $R_3$ =methyl and X=the chiral structure shown in Formula 4.

In this regard, (S)-2,2'-bis(4-pentenamido)-1,1'-binaphthalene was first prepared as above for (S)-2,2-bis(10-undecenamido)-1,1'-binaphthalene using (0.85 g, 8.5 mmole) of 4-pentenoyl chloride in Example 5 rather than 2.5 g of 10-undecenoyl chloride in Example 4. The (S)-2,2'-bis(4-pentenamido)-1,1'-binaphthalene (0.5 g, 32%) was an oil; $^1$H NMR (CD Cl$_3$) δ1.6 (s, 2 H), 2.05 (m, 8 H), 4.6-4.8 (dd, 4 H), 5.3-5.55 (m, 2 H), 6.9-7.1 (m, 2 H), 7.15-7.3 (m, 2 H), 7.4-7.5 (t, 2 H) 7.8-8.1 (m, 4 H), 8.35 (d, 2 H).

The copolymer of Example 5 was prepared exactly as the copolymer of Example 4 except that 0.46 g (1.0 mmole) of (S)-2,2'-bis(4-pentenamido)-1,1'-binaphthalene and 0.28 g (2.1 mmole) of 1,1,3,3-tetramethyldisiloxane Were used in Example 5 rather than 0.40 g of (S)-2,2'-bis(10-undecenamido)-1,1'-binaphthalene and 0.20 g of 1,1,3,3,5,5,7,7-octamethyltetrasiloxane which were used in Example 4. The resulting copolymer (0.55 g, 90%) was a light colored crystalline material.

The preferred procedures to prepare the copolymers in accordance with Formula 1, and which contain molecular cavities, are outlined in Procedure II below and in Example 6 which follows.

PROCEDURE II methylheptakis(2,3-O-methyl)-β-cyclodextrin (compound 6 in Equation 4).

Equation 4

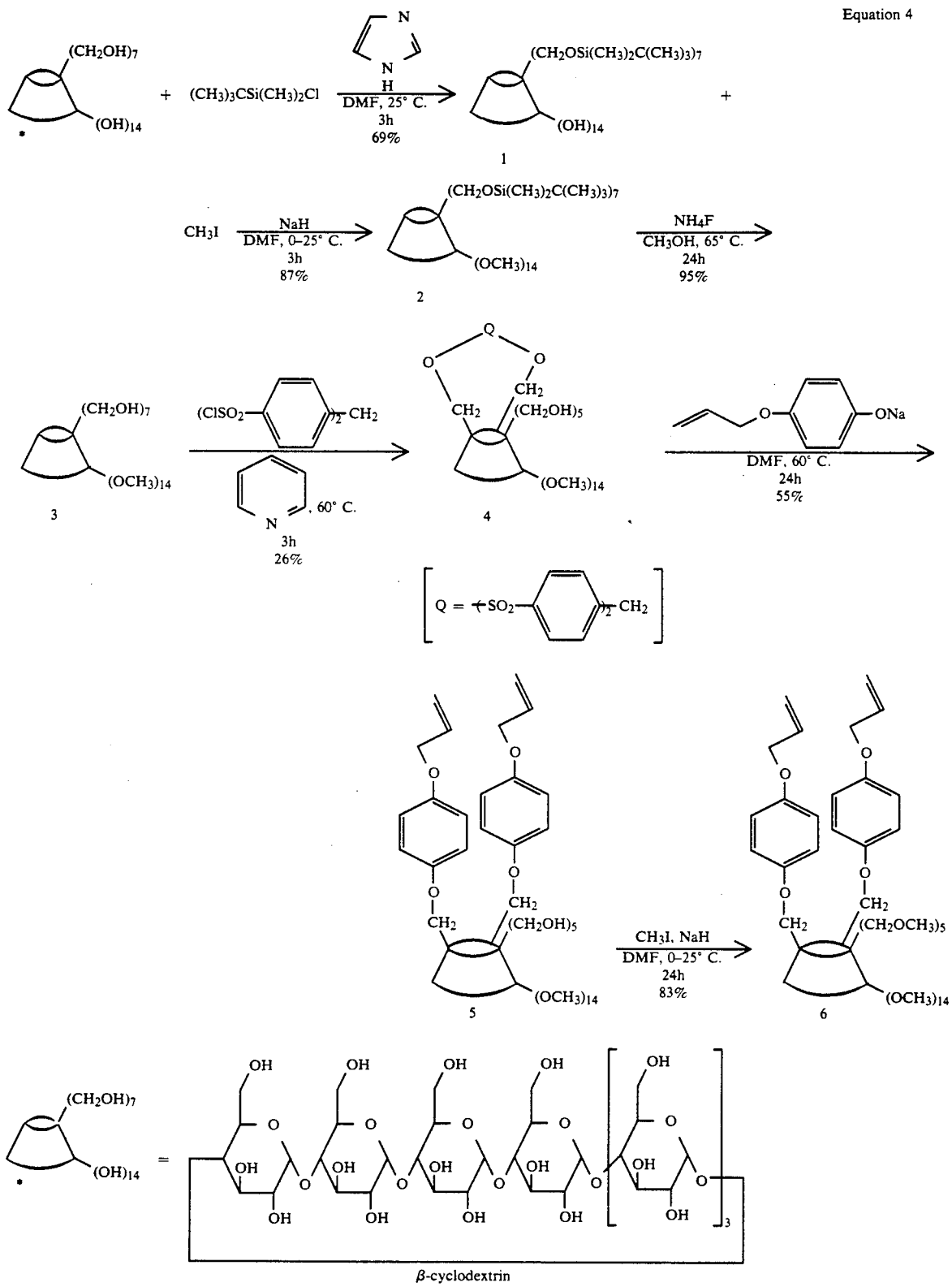

In this procedure, an appropriate dialkene-containing cyclodextrin is first prepared by a sequence of reactions as shown in Equation 4 for the preparation of $6^A,6^C$-(di-O-p-allyloxy-phenyl)-$6^B$, $6^D$, $6^E$, $6^F$, $6^G$-penta-O-

In this regard, tert-butylchlorodimethylsilane or other suitable alcohol protecting group is reacted with β-cyclodextrin in an appropriate solvent such as N,N-dimethylformamide (DMF). An excess of base such as triethylamine or imidazole is used. The reaction mixture is stirred at room temperature for a few hours and can be refluxed for a few hours if necessary to effect the reaction. The mixture is cooled and is usually added to ice water and the solid crude heptakis(6-O-tert-butyldimethylsilyl)-β-cyclodextrin (1 in Equation 4) is filtered, washed with water, and dissolved in a suitable organic solvent such as chloroform or ether. The solvent is washed with cold 3% aqueous hydrochloric acid, then with water, and dried over anhydrous sodium or magnesium sulfate and evaporated. Crude solid product 1 is titurated with hexane, filtered and purified by column chromatography on silica gel using the appropriate mixture of solvents such as chloroform, methanol, and water as eluent.

Compound 1 is reacted with an excess of an appropriate base such as sodium hydride at 0° C. in a suitable solvent such as DMF. An excess of methyl iodide is slowly added to this mixture. The mixture is stirred at 0° C. for a few hours and at room temperature for a few hours and then cooled to 0° C. A suitable proton-containing solvent such as methanol is added to the mixture to decompose the excess sodium hydride. The mixture is evaporated and the residue is dissolved in a suitable solvent such as chloroform or ether. The solution is washed with water, aqueous sodium thiosulfate and water and dried over anhydrous sodium or magnesium sulfate. The solvent is evaporated and crude product heptakis(6-O-tert-butyldimethylsilyl-2,3-di-O-methyl-β-cyclodextrin (2 in Equation 4) is purified by column chromatography on silica gel using the appropriate mixture of solvents such as chloroform, hexane, and ethyl acetate as eluent.

The tert-butyldimethylsilyl protecting group is removed by refluxing a mixture of compound 2 and an excess of ammonium fluoride in methanol for 24 to 36 hours. The mixture is cooled and evaporated. The residue is purified in column chromatography on silica gel using the appropriate mixtures of chloroform and methanol as eluents to give heptakis(2,3-di-O-methyl)-β-cyclodextrin (3).

Compound 3 is placed in a large excess of a suitable solvent such as purified pyridine or toluene and some of the solvent is distilled to remove traces of water. An excess of base such as triethylamine or N-methylmorpholine must be used if pyridine is not the solvent. The solution is cooled to room temperature and a slight excess of a suitable bis(sulfonyl chloride) such as p,p'-methylenebis(benzenesulfonyl chloride) is slowly added. The mixture is stirred until the solid bis(sulfonyl chloride) dissolves and then is stirred at 50°-80° C. for a few hours. The mixture is cooled and the solvent is distilled under reduced pressure. The residue is dissolved in chloroform and the solution was washed with water. The chloroform solution is dried over anhydrous sodium or magnesium sulfate and evaporated. The crude $6^A$, $6^C$-O-[p,p'-methylenebis(benzenesulfonyl)]-heptakis(2,3-di-O-methyl)-β-cyclodextrin (4) is purified by column chromatography using the appropriate mixture of chloroform and methanol as eluent.

Sodium β-allyloxyphenolate is first prepared by reacting a suitable base such as sodium hydride with p-allyloxyphenol. Compound 4 and a slight excess of sodium p-allyloxyphenolate are stirred at 50°-80° C. in a suitable solvent such as DMF for 20-36 hours. The solution is cooled and evaporated. The residue is dissolved in a suitable solvent such as chloroform or ether and the solution is washed with water. The solution is dried over anhydrous sodium or magnesium sulfate and evaporated. The crude $6^A$, $6^C$-(di-O-p-allyloxyphenyl)-heptakis(2,3-di-O-methyl)-β-cyclodextrin (5) is purified by column chromatography on silica gel using an appropriate mixture of chloroform and methanol as eluent.

A mixture of compound 5 and an excess of a suitable base such as sodium hydride in a suitable solvent such as DMF or THF is stirred for a few hours at 0° C. and for 20-40 hours at room temperature. The mixture is cooled to 0° C. and, if sodium hydride is was used, methanol is added to decompose the excess of hydride. The mixture is evaporated and the residue Was dissolved in a suitable solvent such as chloroform or ether. The solution is washed with water, washed with aqueous sodium thiosulfate, and with water. The organic layer is dried over anhydrous sodium or magnesium sulfate and evaporated. The desired $6^A$, $6^C$-bis(O-p-allyloxyphenyl)-$6^B$, $6^D$, $6^E$, $6^F$, $6^G$-penta-O-methyl-heptakis(2,3-di-O-methyl)-β-cyclodextrin (6) is purified by column chromatography using an appropriate mixture of chloroform and methanol as the eluent.

Other chiral dialkene-containing β-cyclodextrins in accordance to Formula 8 and similar to dialkene 6 (Equation 4) but containing O-n-pentyl and mixtures of O-methyl and O-n-pentyl groups are prepared by similar procedures. All of these dialkene-containing β-cyclodextrins are used to prepare copolymers in accordance with Formula 8.

In the second step of Procedure II, the dialkene-containing β-cyclodextrins prepared above are reacted with an oligosiloxane containing a $Si(CH_3)_2H$ unit on each end such as 1,1,3,3,5,5,7,7-octamethyltetrasiloxane (purchased from Petrarch Systems, 2731 Bartram Road, Bristol, PA 19007 and distilled prior to use) or 1,1,3,3,5,5,7,7,9,9,11,11-dodecamethyl-hexasiloxane.

The reaction to form one copolymer in accordance with Formula 1 is given in Equation 5.

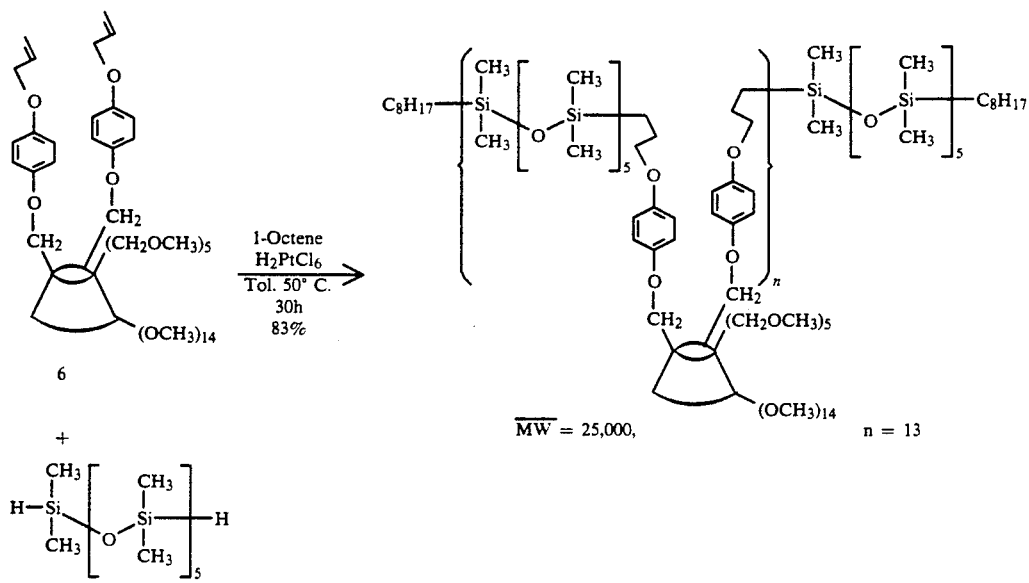

Equation 5

In Equation 5, the oligosiloxane reactant used is 1,1,3,3,5,5,7,7,9,9,11,11,-dodecamethylhexasiloxane. It is possible to use a shorter siloxane analog or other similar analogs or a mixture of analogs for this reaction.

In regard to the reaction shown in Equation 5, a mixture of an excess of the siloxane, platinum catalyst (which can be any suitable platinum material such as hexachloroplatinic acid hydrate or dicyclopentadienyl platinum) a known amount of 1-octene (for end capping purposes to give the correct molecular weight to the copolymer) and 10 mL of toluene are placed in a small Teflon centrifuge tube. The capped tube is heated at about 50° C. in a sonic bath for about 4 hours, the tube is cooled, and the appropriate amount of dialkene-containing β-cyclodextrin is added and the tube is closed and the mixture is heated at 50° C. in a sonic bath until the polymerization reaction is completed (2 to 50 hours). Stirring can be by a magnetic stirring bar. The reaction is followed by observing the decrease in the intensity of the Si-H absorption in infrared spectroscopy. When the bond is no longer seen, the reaction is complete. This takes 2 to 50 hours or even longer. Often, additional platinum catalyst must be added. The toluene is evaporated in a stream of nitrogen or argon gas. The resulting polymer is dissolved in a minimum amount of methylene chloride (usually about 10 mL per gram) and precipitated with methanol or methanol and water. The mixture is centrifuged, the solvents decanted and the precipitate is again dissolved in methylene chloride. This process of dissolution in methylene chloride and precipitation with methanol or methanol and water is repeated 3 or 4 times to ensure separation of the polymer from the unreacted alkene. The polymer is then dissolved in methylene chloride and filtered through a 0.2 mm filter. The solvent is then removed and the polymer is dried under vacuum at 0.1 torr to 1 torr at 50°-60° C. for a period of 10 to 24 hours.

The following example is given to illustrate one molecular cavity containing copolymer which has been made or may be made in accordance with Formula 1 of the present invention. This example is illustrative only and is not comprehensive of the many different copolymers which can be made in accordance with this embodiment.

EXAMPLE 6

In this example, a copolymer gum within the scope of Formula 1 was made wherein m=5, n=3, p=about 13, $R_1$=octyl, $R_2$ and $R_3$ =methyl and X=the cyclodextrin structure shown in Formula 8.

In this regard, $6^A,6^C$-bis(O-p-allyloxyphenyl)-$6^B$, $6^D$, $6^E$, $6^F$, $6^G$-penta -O-methyl-heptakis(2,3-di-O-methyl)-β-cyclodextrin (Compound 6 in Equations 4 or 5) was first prepared by a six-step process as follows. A solution of 12.11 g (80 mmol) of tert-butylchlorodimethylsilane in 60 mL of anhydrous N,N-dimethylformide DMF was added dropwise to a stirred mixture of 11.35 g (10 mmol) of β-cyclodextrin and 10.94 g (0.16 mol) of imidazole in 230 mL of dry DMF during 30 min at room temperature. The mixture was stirred for 2.5 h at room temperature and poured into 1.5 L of ice-water. The precipitate was filtered, washed with water, and dissolved in 500 mL of chloroform. The solution was washed successively with 50 mL of cold 3% aqueous hydrochloric acid, 50 mL of aqueous sodium bicarbonate, and 100 mL of water and dried over anhydrous magnesium sulfate and concentrated. The residue was triturated with 50 mL of hexane, and the resulting white solid was filtered, washed with 10 mL of hexane, and dried. The solid was purified by column chromatography using first, chloroform/methanol=8/1, and then chloroform/methanol/water=50/10/1 as eluents to give 13.4 g (69%) of Compound 1 (see Equation 4); 299°-302° C. (dec.) (from ethanol); $[\alpha]^{25}_D$+247.0 (c=2.2, CHCl$_3$); $^1$H NMR (CDCl$_3$)δ6.71 (s, 7 H, OH), 5.26 (s, 7 H, OH), 4.87 (s, 7 H), 3.45-4.10 (m, 42 H), 0.87 [s, 63 H, C(CH$_3$)$_3$], 0.05 [s, 42 H, Si(CH$_3$)$_2$] $^{13}$C NMR: δ102.0 (C-1), 81.8 (C-4), 73.6, 73.4, and 72.5 (C-2,3,5), 61.7 (C-6), 25.9 [(CH$_3$)$_3$C], 18.3 [(CH$_3$)C], and −5.1 and −5.2 [(CH$_3$)$_2$Si]. Anal. Calcd for [C$_{12}$H$_{24}$O$_5$Si]$_7$: C, 52.14; H, 8.75. Found C, 51.94, H, 8.54.

Sodium hydride (95%, 2.70 g, 107 mmol) was added at 0° C. to a solution of 5.11 g (2.6 mmol) of Compound 1 in 150 mL of DMF and the mixture was stirred for 1 h at 0° C. Methyl iodide (8 mL, 128 mmol) was added dropwise and the mixture was stirred for 1 h at 0° C. The mixture was stirred for 2 h at room temperature and cooled to 0° C. Methanol was added to decompose the excess hydride and the solvents were evaporated under reduced pressure. The residue was partitioned between chloroform and water. The organic layer was separated, washed successively with water, aqueous sodium thiosulfate, and water. The solution was dried and evaporated under reduced pressure. The product was purified by column chromatography (hexane/ethyl acetate=4/1) to give 4.82 g (87%) of Compound 2 (see Equation 4) as an amorphous solid; $[\alpha]^{25}_D +143.0°$ (c =1.45, CHCl$_3$); $^1$H NMR (CDCl$_3$)$\delta$5.16 (d, 7 H), 4.09 (d, 7 H), 3.77–3.40 (m, 70 H), 3.02 (dd, 7 H), 0.88 [s, 63 H, (CH$_3$)$_3$C], and 0.03 [s, 42 H, (CH$_3$)$_2$Si]; $^{13}$C NMR: $\delta$98.1 (C-1), 82.3, 82.0, and 78.6 (C-2, 3, 4), 72.2 (C-5), 62.3 (C-6), 61.4, and 58.6 (OCH$_3$), 25.95 [(CH$_3$)$_3$C], 18.3 [(CH$_3$)$_3$C], and −4.8 and −5.1 [(CH$_3$)$_3$Si]. Anal. calcd for C$_{98}$H$_{196l}$O$_{35}$Si$_7$: C, 55.23; H, 9.27. Found: C, 55.41; H, 9.07.

A solution of 7.20 g (3.4 mmol) of compound 2 and 5.27 g (0.14 mmol) of ammonium fluoride in 125 mL of methanol Was refluxed for 24 h, cooled, and concentrated under reduced pressure. A suspension solution formed by adding 100 mL of ethyl acetate to the above residue was filtered over a 2 cm thick pad of silica gel. The silica gel was placed On top of a silica gel column and eluated with chloroform/methanol=8/1, then chloroform/methanol/water=50/10/1 to give 4.30 g (95%) of heptakis(2,3-di-O-methyl)-β-cyclodextrin Compound 3 (See Equation 4) as a solid; m.p. 153–154° C.; $[\alpha]^{25}_D +193.0°$ (c=1.40, CHCl$_3$). $^1$H NMR (CDCl$_3$): $\delta$5.13 (d, 7 H), 4.41 (s, 7 H, OH), 4.10–3.10 (m, 84 H); $^{13}$C NMR: $\delta$99.35 (C-1), 82.68 (C-4), 82.38 and 82.11 (C-2,3), 72.82 (C-5), 61.68 (C-6), 62.01 and 58.99 (OCH$_3$). Anal. Calcd for [C$_8$H$_{14}$O$_5$]$_7$, C, 50.52; H, 7.42. Found C, 50.36, H, 7.60.

A solution of 5.99 g (4.5 mmol) of 3 in 1,000 mL of dried pyridine was heated under nitrogen and 80 mL of pyridine was distilled to remove traces of water. The solution was cooled to room temperature and 2.0 g (5.4 mmol) of p,p'-methylenebis(benzenesulfonyl chloride) was added slowly. The mixture was stirred until the solid dissolved completely and then it was heated and stirred at 60° C. for 3 h. The mixture was cooled and the pyridine was removed by vacuum distillation (0.2 mm, T<40° C.). The resulting residue was partitioned between chloroform and water. The organic layer was separated, dried over anhydrous magnesium sulfate, and concentrated. The residue was purified by column chromatography (chloroform/methanol=20/1) to give 1.90 g (26%) of Compound 4; m.p. 180–181° C.; $[\alpha]^{25}_D +211.3°$ (c=1.31, CHCl$_3$); $^1$H NMR (CDCl$_3$): $\delta$7.86 (2d, 4 H), 7.52 (2d, 4 H), 5.15 (m, 7 H). 4.09 (s, 4 H), 2.90–3.97 (m, 84 H), 2.09 (s, 5 H, OH); $^{13}$C NMR: $\delta$147.2 (2 C-p,p'), 134.6 and 133.1 (2 C - s,s'), 130.3 and 130.1 (4C - m,m'), 129.5 and 129.1 (4 C-o, o'), 100.2, 99.5, 98.7, and 96.6 (C-1), 82.7 (C-4), 82.4 and 81.7 (C-2,3), 73.5 and 72.5 (C-5), 59.8 and 59.5 (C-6), 62.0 and 58.8 (OCH$_3$), 30.2 (CH$_2$). Anal. Calcd for C$_{69}$H$_{106}$O$_{39}$S$_2$: C, 51.04, H, 6.58. Found C, 50.84, H, 6.47.

A solution of 1.92 g (1.18 mmol) of 4 and 0.81 g (4.72 mmol) of sodium p-allyloxyphenolate was stirred in 100 mL of DMF at 60° C. for 24 h. The residue formed by evaporating the solvent under vacuum was partitioned between 200 mL of chloroform and 100 mL of o water. The organic layer was separated, dried under anhydrous magnesium sulfate, and concentrated. The residue was purified by column chromatography (chloroform/methanol=20/1) to give 1.04 g (55%) of Compound 5 (See Equation 4); m.p. 145°–147° C., $[\alpha]^{25}_D +144.6°$ (c=1.05, CHCl$_3$); $^1$H NMR (CDCl$_3$): $\delta$6.82 (m, 8 H, aromatic), 6.02 (m, 4 H), 5.31 (m, 4 H), 5.07 (m, 7 H), 4.45 (t, 4 H), 4.25 (m, 4 H), 4.07–3.03 (m, 80 H); $^{13}$C NMR: $\delta$153.5 and 153.3 (4 C-s,p), 134.0 (vinyl C), 117.9 (vinyl C), 116.1 and 115.9 (4 C-m,o), 99.4, 99.2, 99.1, and 99.0 (C-1), 82.6, 81.8, and 80.8 (C-4,2,3) 73.0, 72.6, and 72.4 (C-5), 69.8 (CH$_2$), 68.2 and 62.1 (C-6), 61.6 and 59.1 (OCH$_3$—2,3). Anal. Calcd for [C$_{74}$H$_{114}$O$_{37}$]: C, 55.70, H, 7.20. Found C, 55.78; H, 7.24.

Sodium hydride (95%, 240 mg, 7.95 mmol) was added at 0° C. to a solution of 240 mg (0.16 mmol) of Compound 5 in 20 mL of DMF. The mixture was stirred for 1 h at 0° C., stirred for 24 h at room temperature, and cooled to 0° C. Methanol was added to decompose the excess hydride. The mixture was concentrated and the residue was partitioned between chloroform and water. The organic layer was separated, washed successively with water, aqueous sodium thiosulfate, and water. The solution was dried over anhydrous magnesium sulfate and concentrated. The residue was purified by silica gel Chromatography (benzene/ethanol=19/1) to give 222 mg (83%) of 6$^A$,6$^C$-(di-O-p-allyloxyphenyl)-6$^B$,6$^D$,6$^E$,6$^F$,6$^G$-penta-O -methyheptakis(2,3-di-O-methyl)-β-cyclodextrin i.e. compound 6 (See Equation 4); m.p. 125°–126° C.; $[\alpha]^{25}_D +137.2°$ (c=0.96, CHCl$_3$). $^1$H NMR (CDCl$_3$): $\delta$6.82 (m, 8 H, aromatic), 6.00 (m, 2 H), 5.32 (m, 4 H), 5.10 (m, 7 H), 4.44 (m, 4 H), 4.18 (d, 4 H), 4.05–3.10 (m, 95 H); $^{13}$C NMR: $\delta$153.5 (C-s, p, aromatic), 134.0 (vinyl C), 118.0 (vinyl C), 116.0, and 115.9 (C-m, o, aromatic), 99.6 and 99.4 (C-1), 82.6 (C-4), 82.3 and 81.1 (C-2,3), 71.7 and 71.0 (C-5), 69.7 (—CH$_2$—), 68.6 and 59.5 (C-6), 62.0, 59,2, and 58.9 (OCH$_3$—2,3,6). Anal. Calcd for [C$_{79}$H$_{124}$O$_{37}$]: C, 56.96; H, 7.50. Found C, 57.11; H, 7.71.

The copolymer (see Equation 5) was prepared by heating a mixture of 19.5 mg (4.5×10$^{-5}$ mol) of 1,1,3,3,5,5,7,7,9,9,11,11-dodecamethylhexasiloxane, 8 microliters of 1% H$_2$PtCl$_6$ (in THF-ethanol), 1.0 microliters of 1-octene and 10 mL of toluene in a tightly capped 50 mL Teflon centrifuge tube in a sonic bath (Branson 2200) at 50° C. for two hours. The amount of 1-octene used in the reaction was designed to give a final copolymer molecular weight of about 25,000. The heated mixture was cooled and 70 mg (4.2×10$^{-5}$ mol) of 6$^A$,6$^C$-bis(O-p-allyloxyphenyl)-6$^B$,6$^D$,6$^E$,6$^F$, 6$^G$-penta-O-methylheptakis(2,3-di-O-methyl)-β-cyclodextrin (Compound 6) was added. The tube was capped and heated in the sonic bath at 50° C. for 30 h. An infrared spectrum of the mixture showed no Si-H bonds at 2,154 cm$^{-1}$, indicating that the reaction was complete. The toluene was evaporated in a nitrogen gas stream and the copolymer residue was dissolved in 10 mL of methylene chloride, and 10 mL of methanol and 10 mL of water were added. The mixture was centrifuged and the solvents were decanted. The process of dissolution in methylene chloride and precipitation by methanol and water was repeated three more time. The copolymer was dissolved in 10 mL of methylene chloride and filtered through a 0.2 mm filter. The solvent was evaporated giving 74 mg (82%) of brown crystalline copolymer which was dried under vacuum at 60° C. for 10 h. to yield the final copolymer shown in Equation 5.

UTILITY

The copolymers of the present invention have shown utility in connection with stationary phases used in gas and supercritical fluid chromatography. One presently preferred procedure for applying the polymers of the present invention to a chromatographic column is given in Procedure III.

PROCEDURE III

In this procedure, the copolymer to serve as the stationary phase is statically coated in fused silica open tubular columns. The fused silica open tubular columns (for example, about 5-20 meters long and about 25-500 micrometers in inner diameter) are prepared for chromatographic analysis in accordance with the present invention as follows.

First, the fused silica capillaries are purged with dry nitrogen gas at about 250° C. for about four hours before use. The polymer is dissolved in methylene chloride at room temperature at a sufficient concentration to provide a film thickness of about 0.05-0.50 micrometers by the static coating method.

Before filling the fused silica capillaries, the coating solution is carefully filtered through a two-micrometer metal filter device. The columns are then filled with the solution, sealed at one end, and coated with the polymer by evaporating the solvent under vacuum. After coating, the columns are purged with nitrogen gas for about 30 minutes to remove traces of solvent.

The coating of stationary phases thus applied to the fused silica capillaries may next be cross-linked using azo-t-butane as free radical initiator. To achieve such cross-linking, the coated columns are purged with azo-t-butane saturated nitrogen gas. The column ends are then sealed, and the columns are heated from about 40° C. to about 220° C. by increasing the temperature at the rate of about 4° C. per minute and holding at the final temperature of about 220° C. for about 30-40 minutes. After cross-linking, the columns are purged with dry nitrogen gas at room temperature to remove excess azo-t-butane and reaction by-products. The cross-linking reaction can be performed using this and other free radical initiators in a sealed column as set forth in this procedure, or dynamically where the column is purged with an inert gas containing the initiator during the cross-linking reaction. Finally, the columns are rinsed with dry, pure solvent (e.g., pentane or methylene chloride) to remove impurities or soluble polymers (usually low molecular weight) that are not immobilized in the is column.

The following examples are given to illustrate the various silica columns for gas and supercritical fluid chromatography which can be coated with materials made in accordance with Formula 1 of the present invention. These examples are exemplary only, and are not comprehensive of the many different coatings that can be made in accordance with the present invention.

EXAMPLE 7

In this example, the chiral polymer of Example 1 was applied as a stationary phase in a gas chromatographic column. In this regard, an unheated fused silica capillary, about 20 meters long and about 0.2 millimeters in inner diameter (produced by Polymicro Technologies), was water treated and deactivated before it was coated with the chiral polymer. Nitrogen gas was used to push a plug of LC-grade water through the capillary and to dry it at 250° C. for 30 minutes. Deactivation was performed by dynamically coating a film of poly (25% cyanopropyl, 25% hydro) methyl siloxane reagents on the walls of the capillary. The coating solution was about 5% (v/v) in dry acetonitrile, and nitrogen gas was used to push the plug through the capillary and to evaporate the solvents. The capillary ends were carefully flame sealed and the deactivation reaction was performed at 250° C. for 10 h. An overpressure of hydrogen gas in the column was proof of successful reaction. Unreacted deactivation reagent was rinsed out with about 2 mL of methylene chloride.

About 12 mg of the polymer of Example 1 was dissolved in 5 mL of methylene chloride at room temperature. Before filling the s fused silica column, the polymer-containing solution was carefully filtered through a two-micrometer pore metal filter device. The open tubular column was statically coated with the polymeric solution to provide a film thickness of about 0.15 micrometers on the inside of the open tubular column. The column was then purged with nitrogen gas for about 30 minutes to remove all traces of solvent.

The polymer of Example 1, thus applied to the fused silica column was next cross-linked using azo-t-butane. To achieve this, the polymer-coated column was purged with azo-t-butane saturated nitrogen gas for 30 minutes. The column ends were then sealed in a flame, and the column was heated from about 40° C. to about 220° C. by increasing the temperature at a rate of about 4° C. per minute, and holding at the final temperature of about 220° C. for about 30 minutes. After the cross-linking procedure was completed, the open tubular column was purged with dry nitrogen gas at room temperature for about 30 minutes to remove excess azo-t-butane and reaction byproducts. The cross-linked polymer was cured by purging with nitrogen gas and heating the column from about 40° C. to about 220° C. at about 2° C. per minute and holding the upper temperature for about 30 minutes. Finally, the column was rinsed with about 1 ml of filtered n-hexane.

EXAMPLE 8

In this example, the chiral copolymer of Example 1 was applied as a stationary phase in a supercritical fluid chromatographic column. The open tubular column was prepared as in Example 7 except that the column was about 20 meters long and about 0.05 millimeters in inner diameter in Example 8. The capillary was not water treated, but purged with dry nitrogen gas at about 250° C. for 5 h before deactivating, coating and cross-linking. About 16 mg of the polymer of Example 1 was dissolved in about 1 mL of methylene chloride to provide a film thickness of about 0.15 micrometer on the inside of the 0.05 millimeter inner diameter column.

The stationary phases of the present invention can be used in gas, supercritical fluid, and liquid chromatography. Therefore, it is very important to cross-link the stationary phase to assure stability towards mobile phases with strong solvating properties. Cross-linked polymers are also stable over the temperature range which the stationary phases are to be used.

In addition or, as an alternative to, the placing of a coating on the inside surface of the chromatography column, the polymers may also be coated onto particles and used as a solid packing in the column. Such coated particles may be used as solid packing in supercritical fluid, liquid or gas chromatography columns In FIGS. 1-3, chromatograms are illustrated showing separations achieved when a polymer of the present invention is used as a stationary phase in both gas and supercritical fluid chromatography (SFC). In the gas chromatograms illustrated, a Carlo Erba model 5160 gas chromatograph equipped with a flame ionization detector Was used. A Lee Scientific model 601 SFC instrument Was used to record the SFC chromatograms illustrated in FIGS. 2 and 3. FIG. 1 illustrates the usefulness of the stationary phase in Example 7 in gas chromatography and FIGS. 2 and 3 illustrate the usefulness of the stationary phase in Example 7 in supercritical fluid chromatography. The results illustrated by these Figs. show that the new chiral copolymeric phases prepared in Examples 7 and 8 have utility in the separation of enantiomeric mixtures of various organic substances.

Figure 1B:
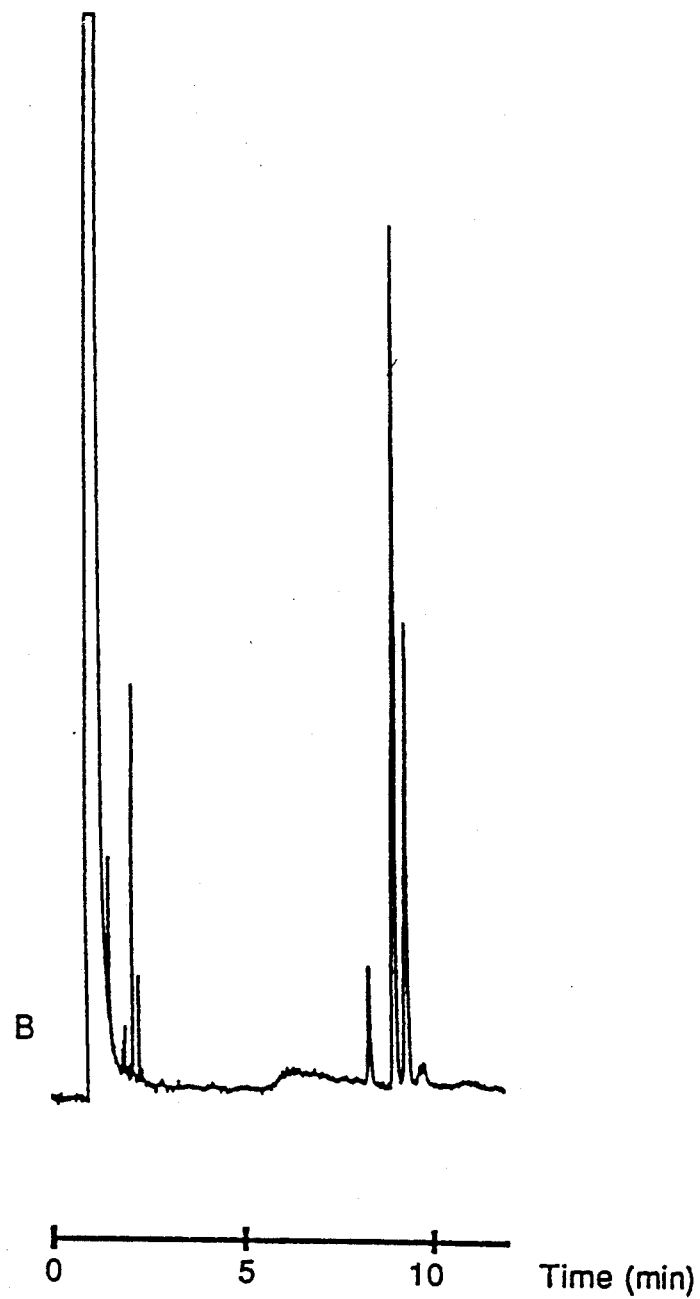

In FIG. 1A and FIG. 1B show chromatograms representing the separation of the (R)- and (S)-forms of the trifluoroacetamide derivatives of α-phenylethylamine (FIG. 1A) and the (R)-and (S)-forms of the pentafluoropropionamide derivatives of α-(1-naphthyl)ethylamine (FIG. 1B) in gas chromatography. The open tubular column for gas chromatography was 20 meters long and about 0.20 millimeters in inner diameter. The polymer of Example 1 was statically coated from methylene chloride solvent to give a film thickness of about 0.15 micrometer on the inside of this column. The α-phenylethylamine derivatives in FIG. 1A eluted after 7 minutes with a selectivity (α) OF 1.08 and an efficiency (N) of about 1,100 at a temperature of 120° C. The α-(i-naphthyl)ethylamine derivatives in FIG. 1B eluted after 9 minutes with a selectivity (α) of 1.04 and an efficiency (N) of about 3,300 at a temperature of 170° C. The increased efficiency and decreased selectivity at the higher elution temperature of 170° C. together results in a slightly lower resolution of the two isomers compared to the resolution at 120° C.

Figure 2A:
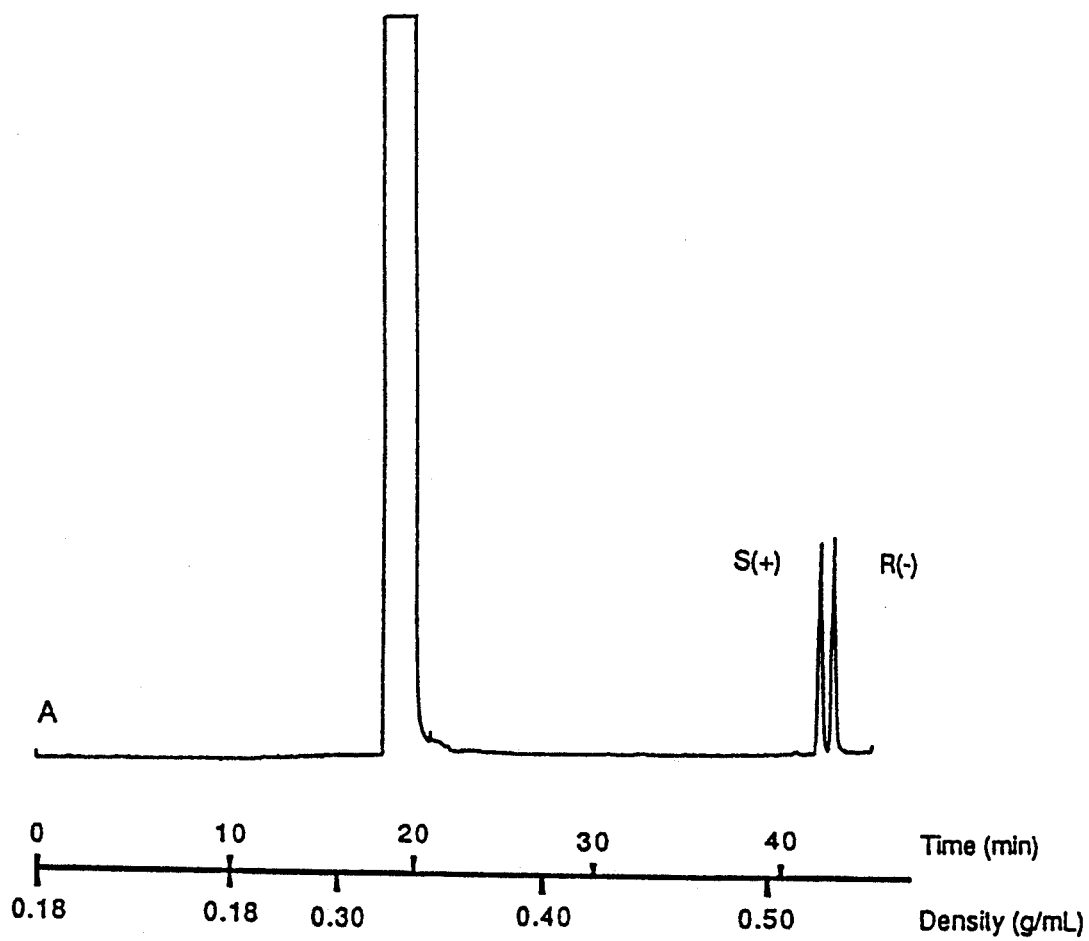
FIGS. 2A, 2B and 2C illustrate supercritical fluid chromatograms wherein ($\pm$)-t-butyl-1,2-ethanediol enantiomers were separated.
Figure 2B:
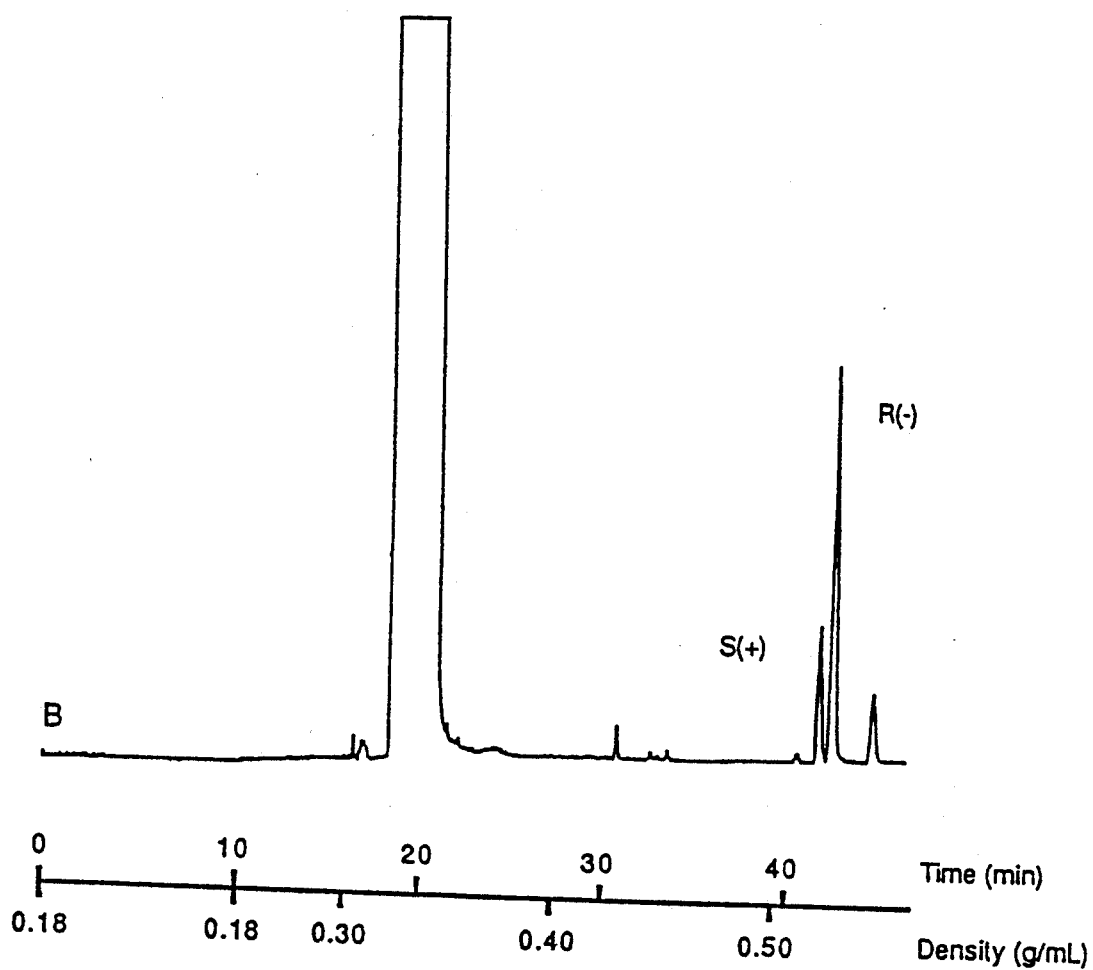
Figure 2C:
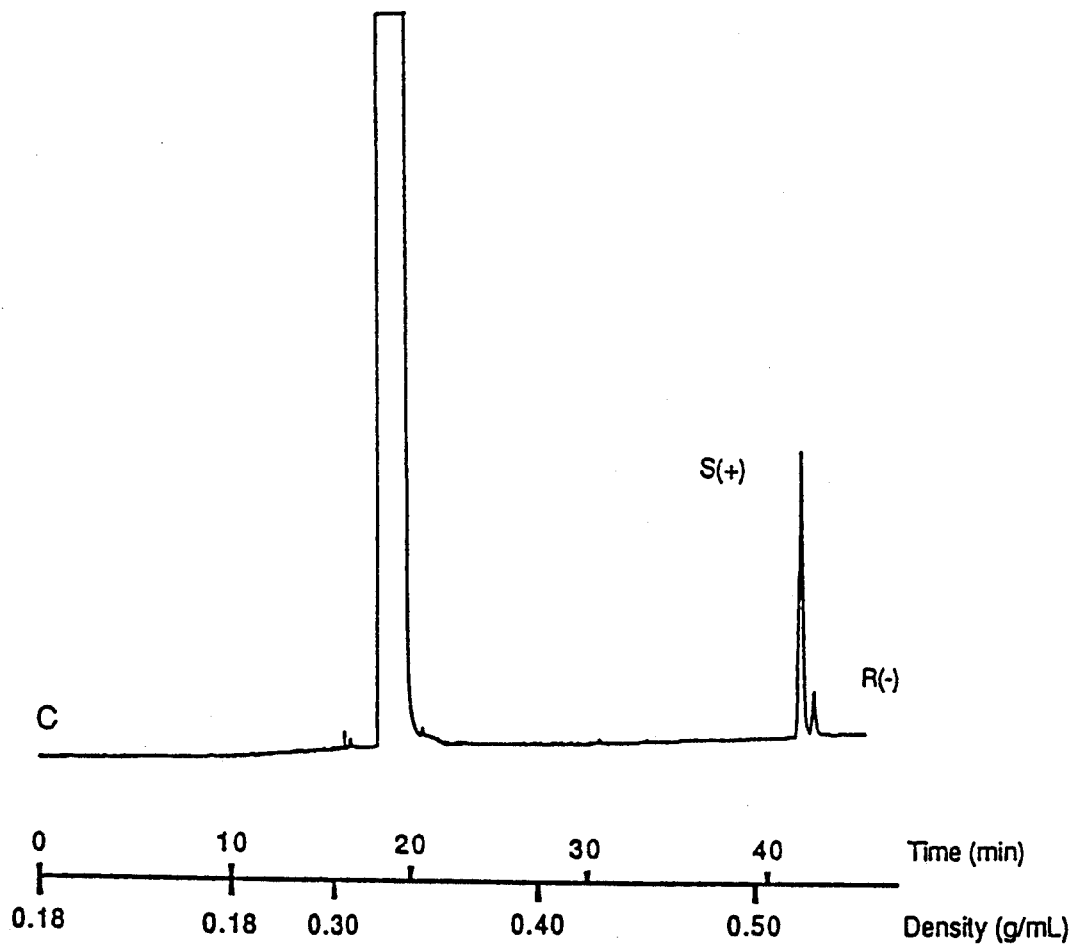
Figure 3:
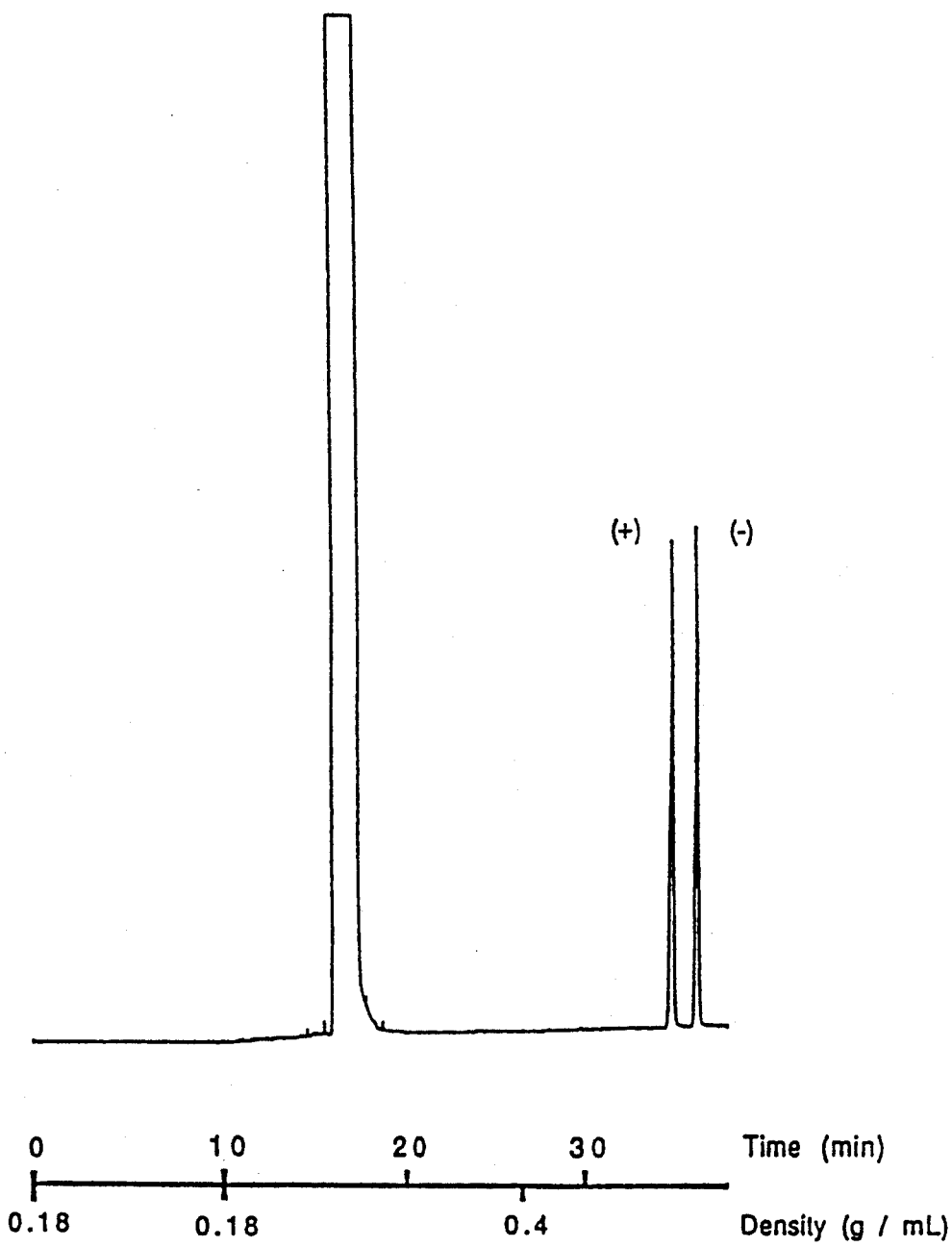

The separation of racemic t-butyl-1,2-ethanediol in SFC using supercritical $CO_2$ is shown in FIGS. 2A, 2B and 2C. The chromatogram of FIG. 2A illustrates the separation of racemic t-butyl-1,2-ethanediol into its two enantiomers. The chromatogram of FIG. 2B illustrates the separation of a crude synthetic mixture and the chromatogram of FIG. 2C illustrates the separation of 75.9±0.4% pure S-(+)-t-butyl-1,2-ethanediol after isolation and purification. A 20 meter long column with 0.05 millimeters inner diameter was coated with a 0.2 micrometer thick film of the chiral copolymer of Example 1 for the separations shown in FIGS. 2A, 2B, and 2C. $CO_2$ was used as mobile phase at a temperature of 50° C. The samples were injected with split injection and detected by flame ionization detection.

The separation of the stereoisomers of racemic diethyl tartarate in SFC using supercritical $CO_2$ is shown in FIG. 3. The same column and conditions were used for this separation as was described in FIG. 2, except that the separation was carried out at 60° C.

EXAMPLE 9

In this example, the chiral polymer of Example 6 was applied as a stationary phase in a supercritical fluid chromatographic column. In this regard, an unheated fused silica capillary, about 10 meters long and about 0.05 millimeters in inner diameter (produced by Polymicro Technologies) was coated. About 12 mg of the polymer of Example 6 was dissolved in 5 mL of methylene chloride at room temperature. Before filling the fused silica column, the polymer-containing solution was carefully filtered through a two-micrometer pore metal filter device. The open tubular column was statically coated with the polymeric solution to provide a film thickness of about 0.15 micrometers on the inside of the open tubular column. The column was then purged with nitrogen gas for about 30 minutes to remove all traces of solvent.

In FIGS. 4-7, chromatograms are illustrated showing separations achieved when a polymer of the molecular cavity embodiment of present invention is used as a stationary phase in supercritical fluid chromatography (SFC). A Lee Scientific model 601 SFC instrument was used to record the SFC chromatograms illustrated in FIGS. 4-7. FIGS. 4-7 illustrate the usefulness of the stationary phase in Example 8 in SFC. The results illustrated by these figures show that the new chiral copolymeric phases prepared in Example 6 have utility in the separation of enantiomeric mixtures of various organic substances.

Figure 4:
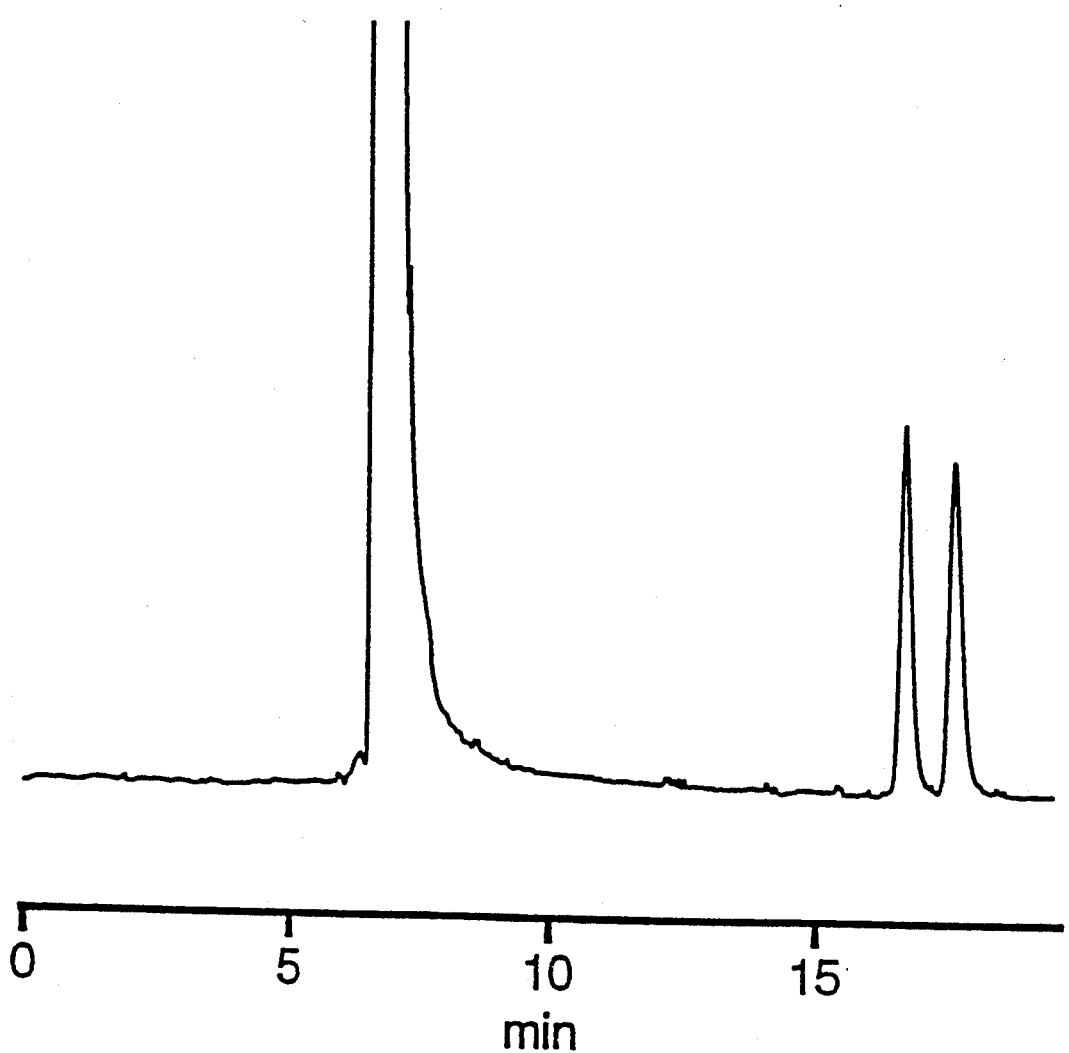
FIG. 4 illustrates a supercritical fluid chromatogram wherein enantiomers of the diethyl tartrate were separated.

FIG. 4 shows the chromatogram representing the separation of the (+) and (−) forms of diethyl tartarate in SFC. A 10 meter long column with about 0.05 millimeters inner diameter was coated with about a 0.15 micrometer thick film of the chiral cavity-containing copolymer of Example 6 in the separations shown in FIGS. 4-7. $CO_2$ was used in the mobile phase at a temperature of 60° C. The samples were injected with split injection and detected by flame ionization detection. For the separation of the enantiomers of diethyl tartarate shown in FIG. 4, the chromatograph was programmed from 0.30 grams per milliliter to 0.50 grams per milliliter at 0.01 grams per milliliter per minute.

Figure 5:
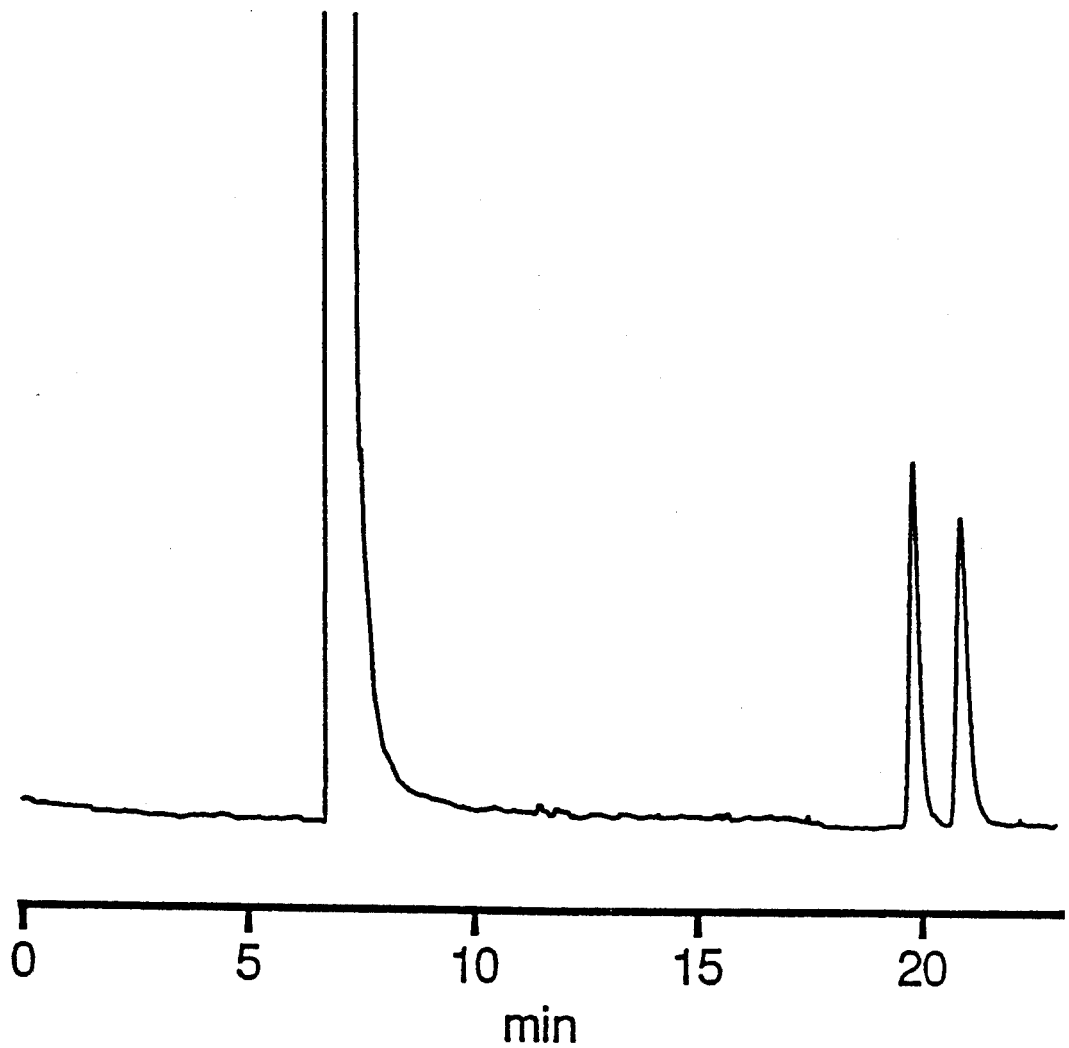
FIG. 5 illustrates a supercritical fluid chromatogram showing the separation of the enantiomers of racemic 2,4-pentanediol.

FIG. 5 shows the chromatogram representing the separation of the (+) and (−) forms of 2,4-pentanediol in SFC using supercritical $CO_2$ at 60° C. The chromatograph was programmed from 0.20 grams per milliliter to 0.50 grams per milliliter at 0.01 grams per milliliter per minute.

Figure 6:
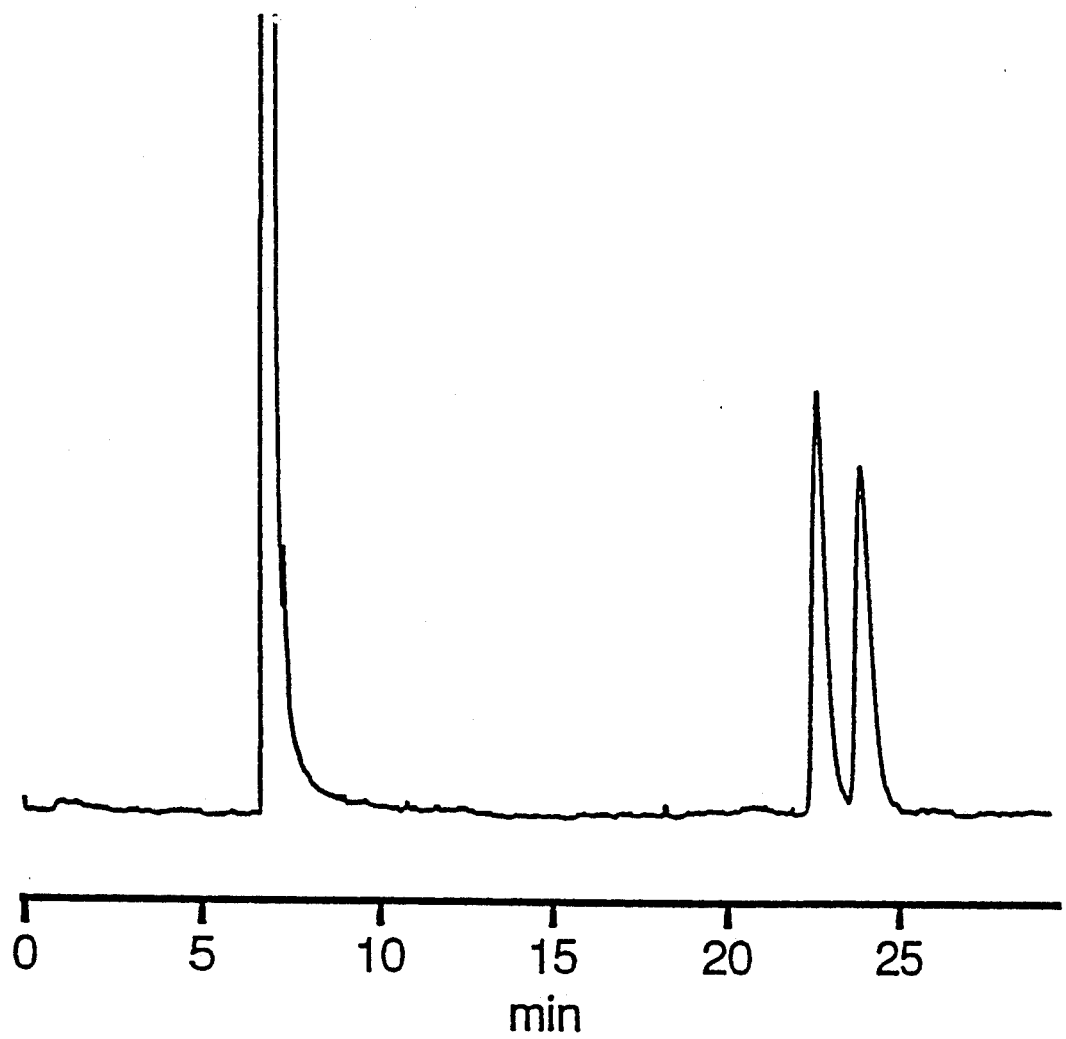
FIG. 6 illustrates a supercritical fluid chromatogram of racemic 1,2-cyclohexanediol.

FIG. 6 shows the chromatogram representing the separation of the (+) and (−) forms of 1,2-cyclohexanediol in SFC using supercritical $CO_2$ at 60° C. The chromatograph was programmed as described in FIG. 4.

Figure 7:
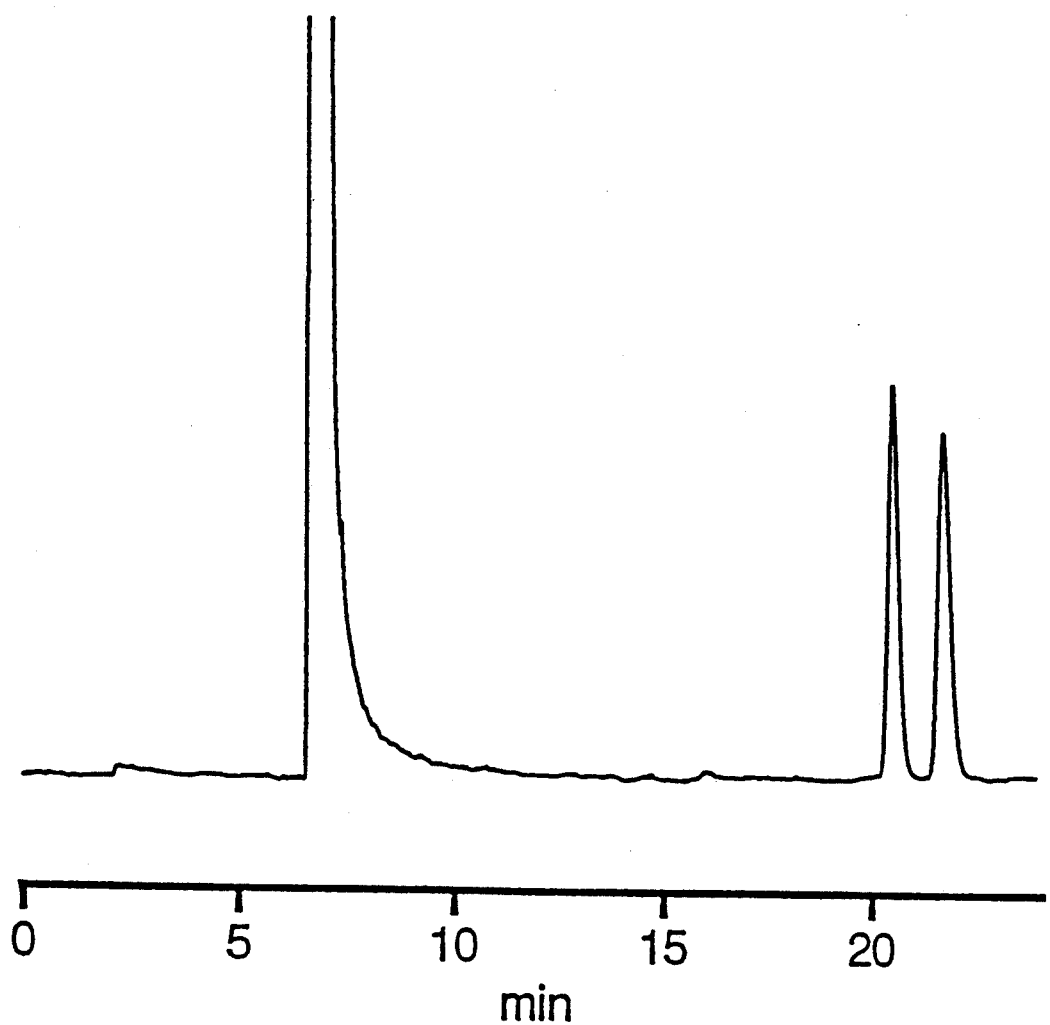
FIG. 7 illustrates a supercritical fluid chromatogram of racemic 2-phenylcyclohexanol.

FIG. 7 shows the chromatogram representing the separation of the (+) and (−) forms of 2-phenylcyclohexanol in SFC using supercritical $CO_2$ at 60° C. The chromatograph was programmed as described in FIG. 4.

From the foregoing, it will be appreciated that the polymers of the present invention provide stationary phases which achieve chromatographic separation Of enantiomers With high chromatographic efficiency and selectivity. The polymers of the present invention have utility over a wide temperature range and with supercritical fluid mobile phases. It is therefore possible to utilize the inherent selectivity that the phase has at low temperature since the temperature can be chosen as an independent parameter in SFC in contrast to gas chromatography. Moreover, since the polymers of the present invention separate compounds with and without aromatic rings and are compatible with supercritical fluids and low temperature use, they will provide separation of a wide range of compounds with sensitive universal detection in supercritical fluid chromatography not possible with liquid chromatography.

The present invention may be embodied in other specific forms without departing from its spirit or essential characteristics. The described embodiments are to be considered in all respects only as illustrative and not restrictive. The scope of the invention is, therefore, limited only by the appended claims rather than by the foregoing description. All changes which come within the meaning and range of functional equivalency of the claims are to be embraced within their scope.

We claim:

1. A compound of for achieving chromatographic separations of stereoisomeric forms of various organic compounds from a mixture thereof said compound having the formula

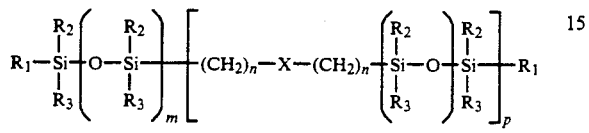

wherein m is an integer from 1 to about 12, n is an integer from 0 to about 16 and p is an integer from 1 to about 100; $R_1$, $R_2$ and $R_3$ are selected from the group consisting of lower alkyl, phenyl, phenyl lower alkyl and substituted derivatives thereof and X is any enantiomerically enriched organic grouping which is uniform in structure and stereochemically configured so as to discriminate on the basis of shape such that one stereoisomer of a stereoisomeric mixture interacts more strongly with said compound than other stereoisomers in said mixture and which is chemically and thermally stable to gas, liquid or supercritical fluid chromatographic conditions.

2. A compound as defined in claim 1 wherein X is chiral.

3. A compound as defined in claim 2 wherein X is an organic grouping containing one or more combinations of organic moieties selected from the group consisting of methylene, phenylene, naphthylene, biphenylene, binaphthylene, a cyclodextrin and cycloalkylydene and substituted derivatives thereof.

4. A compound as defined in claim 3 wherein X also includes non-metal atoms and functional groups which act as linking agents for the organic moieties and are selected from the group consisting of ethers, thioethers, amines, carbonyls, amides, esters, sulfoxides, sulfonates, thioamides, thioesters, ureas, thioureas, carbamates, thiocarbamates, phosphines and phosphine oxides.

5. A compound as defined in claim 4 Wherein the total number of atoms possessed by X does not exceed 300.

6. A compound as defined in claim 5 wherein X is an organic grouping containing one or more combinations of organic moieties selected from the group consisting of methylene, phenylene, naphthylene, biphenylene and binaphthylene and substituted derivatives thereof.

7. A compound as defined in claim 6 wherein X is a member selected from the group consisting of wherein Bz is benzoyl and Ph is phenyl

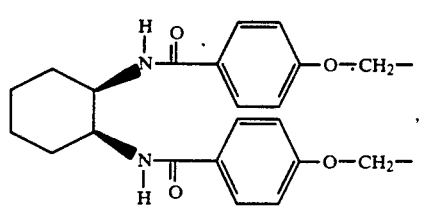

-continued

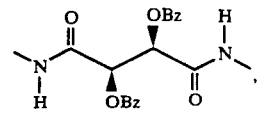

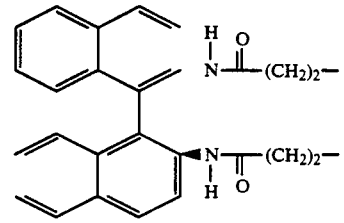

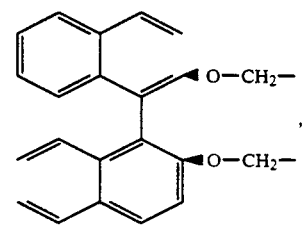

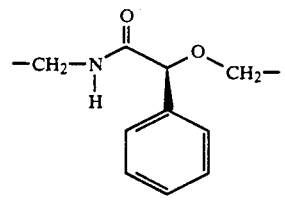

and

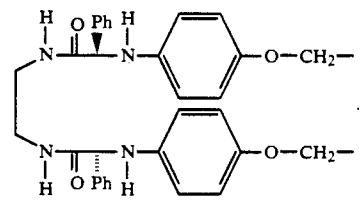

8. A compound as defined in claim 7 wherein m is an integer of between 1 and about 5, n is an integer between 2 and about 10 and p is an integer of between about 35 and 50.

9. A compound as defined in claim 8 wherein $R_1$, $R_2$ and $R_3$ are lower alkyl.

10. A compound as defined in claim 9 wherein n is an integer of 2 or 8, m is an integer of 1 or 3.

11. A compound as defined in claim 10 wherein $R_1$ is octyl and $R_2$ and $R_3$ are each methyl.

12. A compound as defined in claim 10 wherein X is a member selected from the group Consisting of

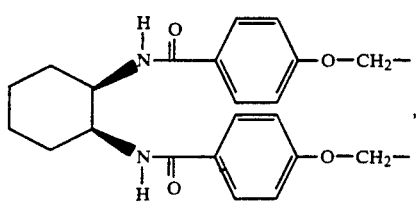

-continued

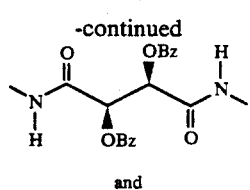

and

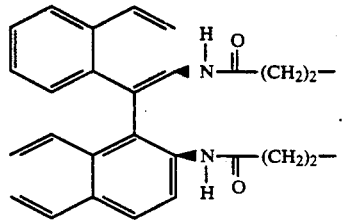

wherein Bz is benzoyl.

13. A compound as defined in claim 12 wherein m is 3, n is 2, p is about 42 and X is

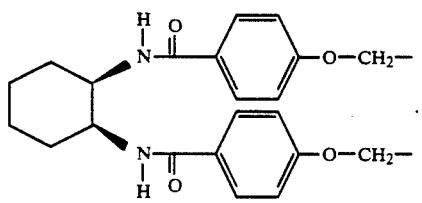

14. A compound as defined in claim 12 wherein m is 1, n is 2, p is about 46 and X is

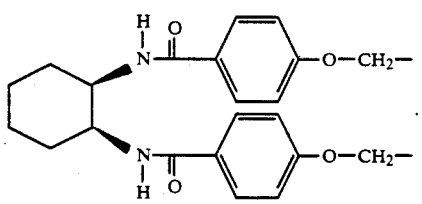

15. A compound as defined in claim 12 wherein m is 3, n is 2, p is about 40 and X is

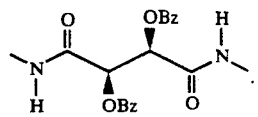

wherein Bz is benzoyl.

16. A compound as defined in claim 12 wherein m is 3, n is 8, p is about 36 and X is

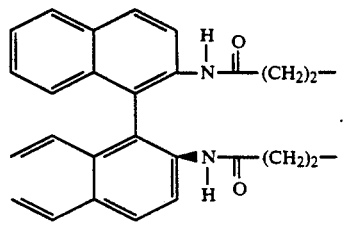

17. A compound as defined in claim 12 wherein m is 1, n is 2, p is about 40 and X is

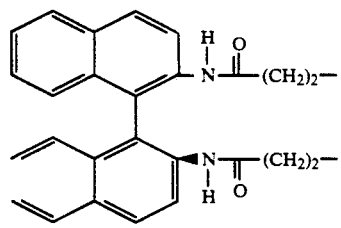

18. A compound as defined in claim 5 wherein X is an organic grouping containing one or more combinations of organic moieties selected from the group consisting of biphenylene, binaphthylene, a cyclodextrin and cycloalkylydene and substituted derivatives thereof.

19. A compound as defined in claim 18 wherein X is a member selected from the group consisting of

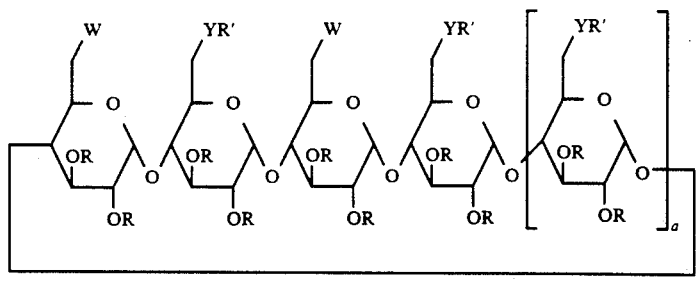

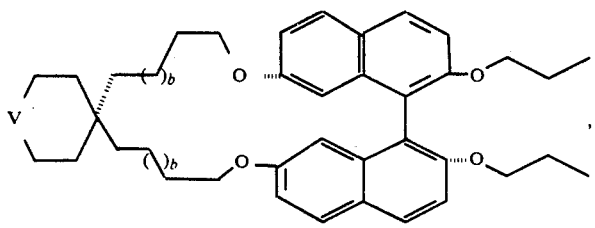

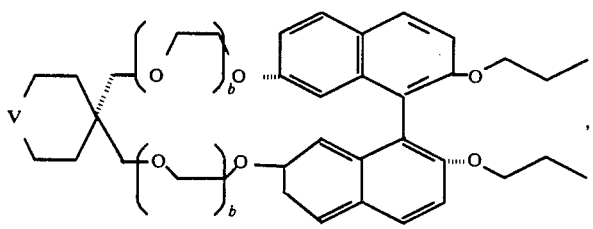

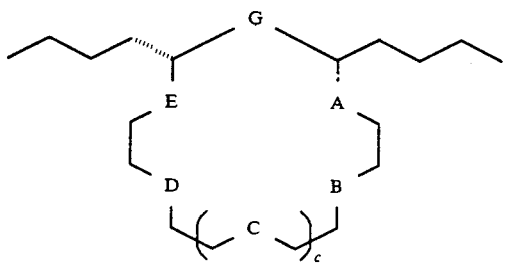

and

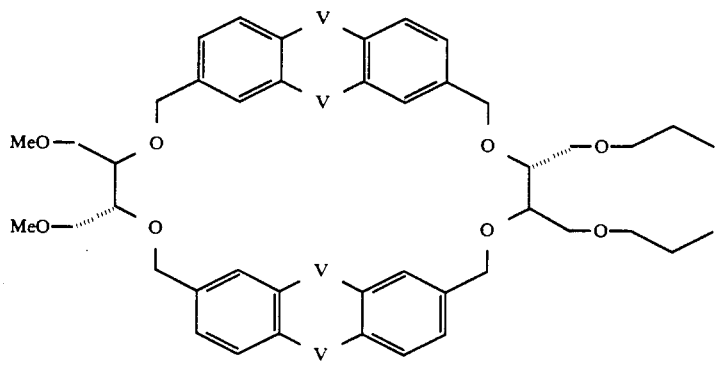

where R is a member selected from the group consisting of H, alkyl, aryl and aralkyl; W is a member selected from the group consisting of O, S, O—Ar—O, S—Ar—S, S—Ar—O, O—Ar—S, O—Ar, S—Ar, NHC(O), NHC(S), N(R'), N(R')—Ar—O, N(R')S, N(R')—Ar, NHC(O)—Ar—O, NHC(O)—Ar, NHC(O)—Ar—S, O—Ar—NH-C(O), and S—Ar—NHC(O), where Ar is an aromatic ring selected from the group consisting of phenylene, pyridylene, and furanylene; R' is a member selected from the group consisting of H, alkyl, aryl and aralkyl; Y is a member selected from the group consisting of O, OC(O), S, SC(S), NHR', NHC(O), and NHC(S); a is an integer of from 2 to 4; V is a member selected from the group consisting of $CH_2$, O, S, NR", C(O), NC(O)R", and NC(S)R" where R" is a member selected from the group consisting of H, alkyl, aryl and aralkyl; b is an integer of from 0 to 10;; A—E can be any member, or combination of members, selected from the group consisting of O, $CH_2O$, S, $CH_2S$, NR" and $CH_2NR$" where R" is as defined above; G is a member selected from the group consisting of $CH_2OCH_2$, $CH_2SCH_2$, $CH_2N(R")CH_2$, phenylene, pyridylene and furanylene and c is an integer of from 0 to 6.

20. A compound as defined in claim 19 wherein m is an integer of between 1 and about 5, n is an integer between 2 and about 10 and p is an integer of between about 10 and 30.

21. A compound as defined in claim 20 wherein $R_1$, $R_2$ and $R_3$ are lower alkyl.

22. A compound as defined in claim 21 wherein $R_1$ is octyl and $R_2$ and $R_3$ are each methyl.

23. A compound as defined in claim 22 wherein n is an integer of 3, m is an integer of 5.

24. A compound as defined in claim 21 wherein X is a cyclodextrin member of the formula

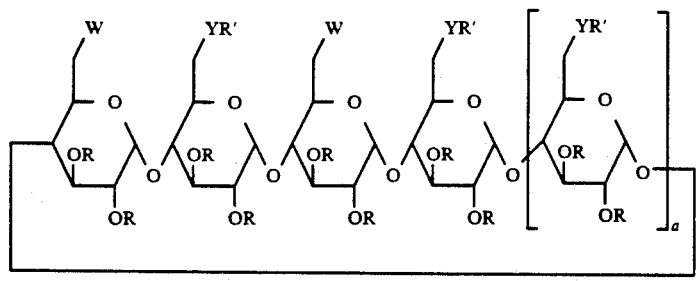

where R is a member selected from the group consisting of H, alkyl, aryl and aralkyl; W is a member selected from the group consisting of O, S, O—Ar—O, S—Ar—S, S—Ar—O, O—Ar—S, O—Ar, S—Ar, NHC(O), NHC(S), N(R')—Ar, NHC(O)—Ar—O, NHC(O)—Ar, NHC(O)—Ar—S, O—Ar—NHC(O), and S—Ar—NHC(O), where Ar is an aromatic ring selected from the group consisting of phenylene, pyridylene, and furanylene; R' is a member selected from the group consisting of H, alkyl, aryl and aralkyl; Y is a member selected from the group consisting of O, OC(O), S, SC(S), NHR', NHC(O), and NHC(S) and a is an integer of from 2 to 4.

25. A compound as defined in claim 24 where R is alkyl; W a member selected from the group consisting of —O—p—$C_6H_4O$—, —NHC(O)—p—$C_6H_4O$—, and —NHC(O)—pp13 $C_6H_4$—; YR' is O-alkyl and a is 3.

26. A compound as defined in claim 25 wherein m is 5, n is 3, and p is about 13.

27. A compound as defined in claim 26 where X is

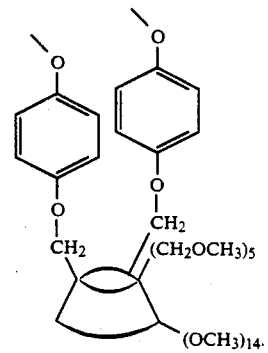

* * * * *